United States Patent [19]
Iida et al.

[11] Patent Number: 5,808,018
[45] Date of Patent: Sep. 15, 1998

[54] FLUORINE CONTAINING SIALYL LEWIS X DERIVATIVES AND SYNTHETIC INTERMEDIATES THEREOF

[75] Inventors: Takao Iida; Yutaka Ohira, both of Tsukuba, Japan

[73] Assignee: Daikin Industries, Ltd., Osaka, Japan

[21] Appl. No.: 809,931

[22] PCT Filed: Aug. 8, 1996

[86] PCT No.: PCT/JP96/02250

§ 371 Date: Apr. 3, 1997

§ 102(e) Date: Apr. 3, 1997

[87] PCT Pub. No.: WO97/08207

PCT Pub. Date: Mar. 6, 1997

[30] Foreign Application Priority Data

Aug. 9, 1995 [JP] Japan .................................. 7-203242

[51] Int. Cl.$^6$ .......................... C07H 15/00; A61K 31/70
[52] U.S. Cl. .................... 536/17.2; 536/4.1; 536/17.9; 536/18.4; 536/18.7; 536/122; 536/124; 514/25; 514/54; 514/61; 514/62
[58] Field of Search .................... 536/4.1, 17.2, 536/17.9, 18.4–18.7, 122, 124; 514/25, 54, 61, 62

[56] References Cited

U.S. PATENT DOCUMENTS 5,374,746 12/1994 Ok et al. .................................. 549/417
5,646,123  7/1997 Ippolito et al. ............................ 514/25

FOREIGN PATENT DOCUMENTS

WO 9219632  11/1992  WIPO.

OTHER PUBLICATIONS

Korytnyk et al. *Tetrahedron* 1982, 38(16), 2547–2550.
Mulligan et al., Nature, 364(Jul. 1993) 149–151.
Stahl et al., Angew. Chem. Int. Ed. Engl., 33(1994) 2096–1098.

Butchard et al., Tetrahedron, 35(1979), pp. 2551–2554.

Nicolaou et al., Carbohydrate Research, 202(1990) 177–191.

Kameyama et al., Carbohydrate Research, 200(1990) 269–285.

Biochemistry, 36:823–831 (1997); Murray et al.

Bioorganic & Medicinal Chemistry, 5(2):383–391 (1997); Baisch et al.

*Primary Examiner*—Kathleen K. Fonda
*Attorney, Agent, or Firm*—Birch, Stewart, Kolasch & Birch, LLP

[57] ABSTRACT

A sialyl Lewis X derivative represented by the general formula:

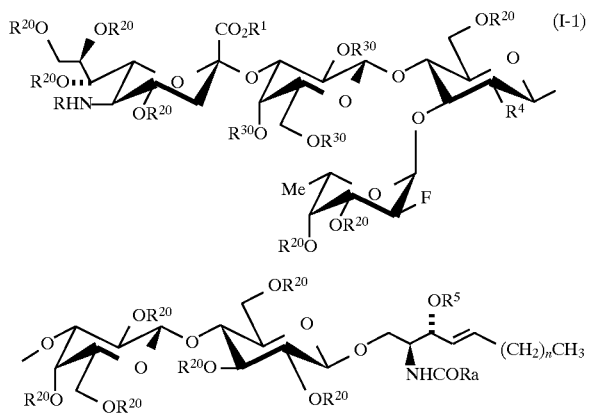

in which a hydroxyl group at the 2 position of fucose is replaced with a fluorine atom, and a synthetic intermediate therefor are provided.

8 Claims, No Drawings

FLUORINE CONTAINING SIALYL LEWIS X DERIVATIVES AND SYNTHETIC INTERMEDIATES THEREOF

The present application is the U.S. National Phase entry under 35 U.S.C. §371, of PCT/JP96/02250 filed on Aug. 8, 1996.

FIELD OF THE INVENTION

The present invention relates to sialyl Lewis X derivatives in which the hydroxy group at the 2 position of fucose is substituted with fluorine, and synthetic intermediates thereof and a process for the preparation thereof. These derivatives are useful in the fields of medical drugs, for example, in the fields of the treatment and prophylaxis of inflammation and thrombopoiesis associated with inflammation, asthma, rheumatism, immunological diseases and cancers.

BACKGROUND OF THE INVENTION

Sialyl Lewis X sugar chain, which is an oligosaccharide containing fucose, has recently attracted attention since it may be involved in homing phenomena in which upon inflammation leucocytes interact with endotheliocytes of blood vessels and bleed out of the blood vessels. Some of the homing phenomena start with interaction of the sialyl Lewis X oligosaccharide with a lectin-like cell adhesive molecule called selectin. Therefore, if the sialyl Lewis X oligosaccharide could be used as a selectin binding inhibitor, acute inflammations depending upon neutrophils (one of leucocytes) and upon selectin would be expected to be suppressed. In fact, is was shown by a group of Michigan University that acute pulmonic inflammation caused experimentally in rat using cobra venom factor was relieved by administration of the sialyl Lewis X sugar chain (M. S. Mulligan, et al., Nature, 364, 149 (1993)).

Thus, synthesis of various derivatives, for example, derivatives (3) (S. Hakomori, et al., WO 92/19632 (1992)) and (4) (W. Stahl, et al., Angew. Chem. Int. Ed. Engl., 33, 2096 (1994)) in which hydrogen atoms or hydroxy groups of Lewis X ganglioside (1) or sialyl Lewis X ganglioside (2) are replaced by fluorine, were studied. However, it is considered that these derivatives would lose their activity immediately since fucose is released due to α-1,3-fucosidase.

Accordingly, we have made an attempt to create a sialyl Lewis X having potent selectin adhesion inhibiting activity and metabolic stability. As such a candidate compound, a derivative of sialyl Lewis X in which a hydroxy group at the 2 position of fucose is substituted with a fluorine atom was designed. There was no method for introducing such a fluorine-containing fucose into the sugar chain streo- and position-specifically.

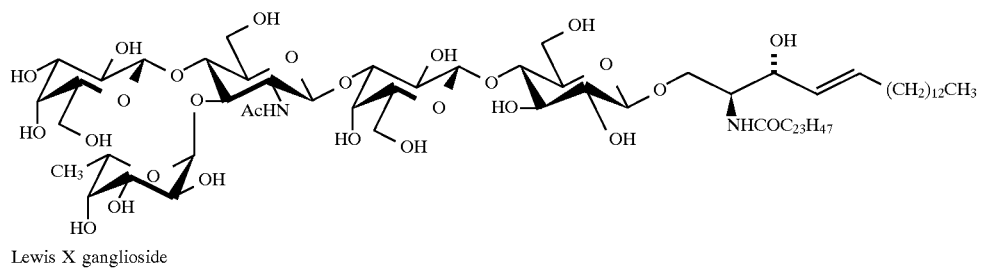

Lewis X ganglioside

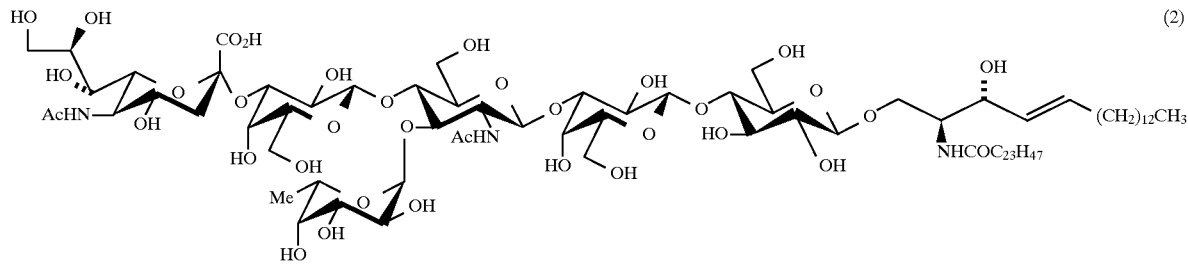

Sialyl Lewis X ganglioside

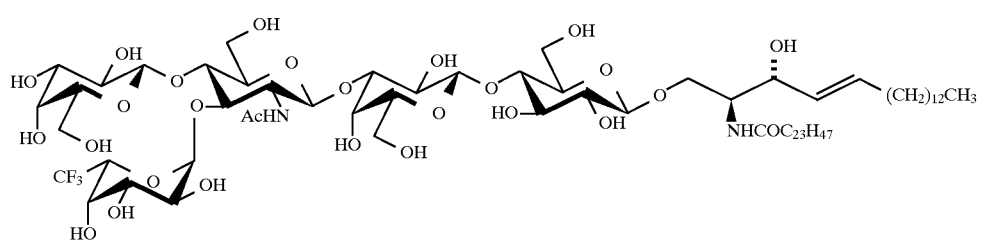

-continued

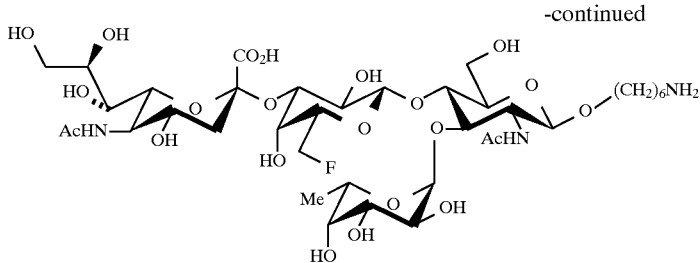
(4)

Sialyl Lewis X derivatives are known to be ligand moieties of E and L selectins having an action as a cell adhesion molecule, and are important compounds having a function as a recognition element of cells specifically expressing these selecting. It is useful to synthesize sialyl Lewis X derivatives modified with fluorine in an organic chemical manner so as to investigate the effects of chemical structures on the expression of their activity. It is also considered that such a fluorine-substituted sialyl Lewis X could be applicable to development of practical medical drugs and clinic.

Therefore, it is very meaningful to elucidate the above described sialyl Lewis X derivatives and to provide them in practical amounts.

SUMMARY OF THE INVENTION

It is an object of the present invention to provide new fluorine-containing sialyl Lewis X derivatives which are expected to be the above described drugs, synthetic intermediates thereof and a method of their preparation.

The present inventor has studied for the purpose of synthesizing sialyl Lewis X analogs in which a hydroxy group at the 2 position of fucose is chemically modified with fluorine and, as a result, succeeded in the synthesis of such analogs leading to the present invention.

Accordingly, the present invention relates to a sialyl Lewis X derivative represented by the general formula (I-1):

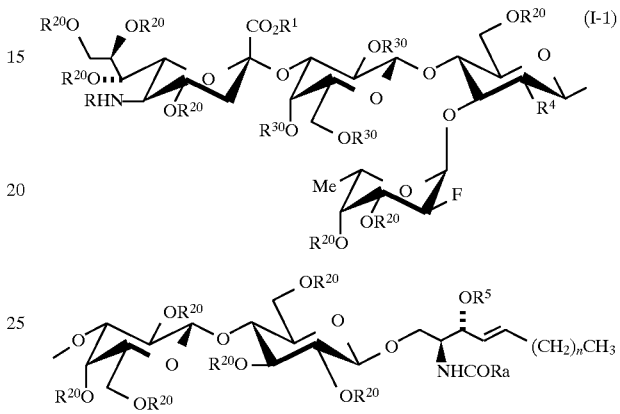

wherein R denotes an aliphatic acyl group having 2 to 6 carbon atoms; $R^1$ denotes a hydrogen atom or a lower alkyl group having 1 to 5 carbon atoms; $R^{20}$, $R^{30}$ and $R^5$ independently denote a hydrogen atom, an aliphatic acyl group having 2 to 6 carbon atoms, or an aromatic acyl group having 7 to 13 carbon atoms; $R^4$ denotes a hydroxy group, an aliphatic acylamino group having 2 to 6 carbon atoms, an aromatic acylamino group having 7 to 13 carbon atoms, an aliphatic acyloxy group having 2 to 6 carbon atoms, or an aromatic acyloxy group having 7 to 13 carbon atoms; Ra denotes a straight or branched, saturated or unsaturated, aliphatic group having 1 to 30 carbon atoms; Me denotes a methyl group; and n denotes an integer of 0 to 20, provided that when $R^1$ is a hydrogen atom, $R^{20}$, $R^{30}$ and $R^5$ all denote a hydrogen atom; and $R^4$ denotes a hydroxy group, or an aliphatic or aromatic acylamino group; or when $R^1$ is a lower alkyl group, $R^{20}$, $R^{30}$ and $R^5$ denote an aliphatic or aromatic acyl group; and $R^4$ denotes an aliphatic or aromatic acylamino group, or an aliphatic or aromatic acyloxy group.

The present invention also relates to a compound represented by the general formula (I-2):

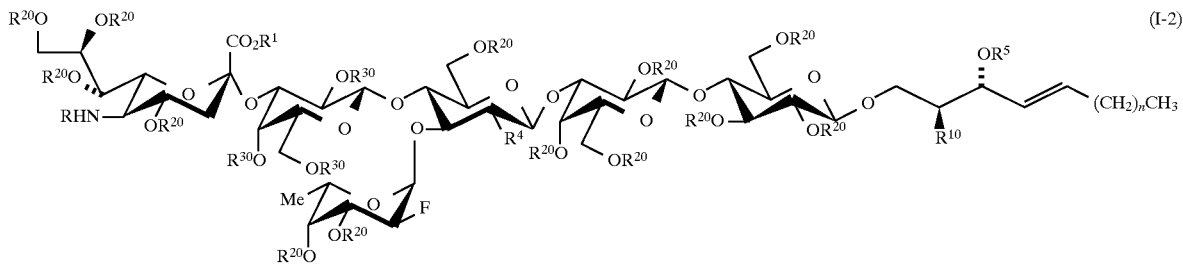

wherein R, $R^1$, $R^{20}$, $R^{30}$, $R^4$, $R^5$, Me and n are as defined above; and $R^{10}$ denotes $N_3$ or $NH_2$ group, provided that when $R^1$ is a hydrogen atom, $R^{20}$, $R^{30}$ and $R^5$ all denote a hydrogen atom; and $R^4$ denotes a hydroxy group, or an aliphatic or aromatic acylamino group; or when $R^1$ is a lower alkyl group, $R^{20}$, $R^{30}$ and $R^5$ denote an aliphatic or aromatic acyl group; and $R^4$ denotes an aliphatic or aromatic acylamino group, or an aliphatic or aromatic acyloxy group, which compound is a synthetic intermediate of the compound represented by the general formula (I-1).

The present invention also relates to a compound represented by the general formula (II):

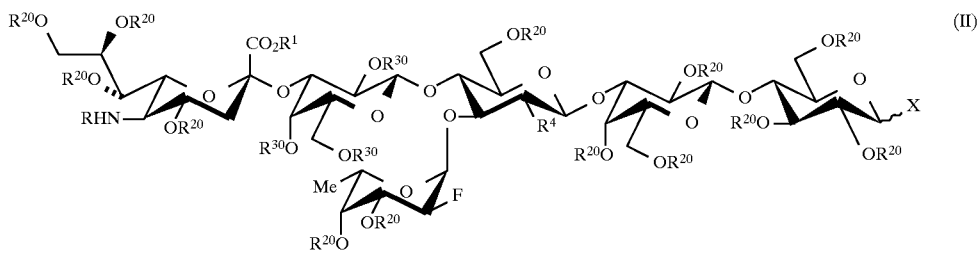

wherein R, $R^1$, $R^{20}$, $R^{30}$, $R^4$ and Me are as defined above; and X denotes a hydroxy group, a fluorine atom, a thioalkyl group having 1 to 5 carbon atoms, a thioaryl group having 6 to 12 carbon atoms, or a —OC(NH)CCl$_3$ group, provided that when $R^1$ is a hydrogen atom, $R^{20}$ and $R^{30}$ both denote a hydrogen atom; $R^4$ denotes a hydroxy group, or an aliphatic or aromatic acylamino group; and X denotes a hyroxy group; or when $R^1$ is a lower alkyl group, $R^{20}$ and $R^{30}$ denote an aliphatic or aromatic acyl group; $R^4$ denotes an aliphatic or aromatic acylamino group, or an aliphatic or aromatic acyloxy group; and X denotes a fluorine atom, a thioalkyl group, a thioaryl group or a —OC(NH)CCl$_3$ group, which compound is a synthetic intermediate of the compound represented by the general formula (I-2).

Further, the present invention relates to a compound represented by the general formula (III):

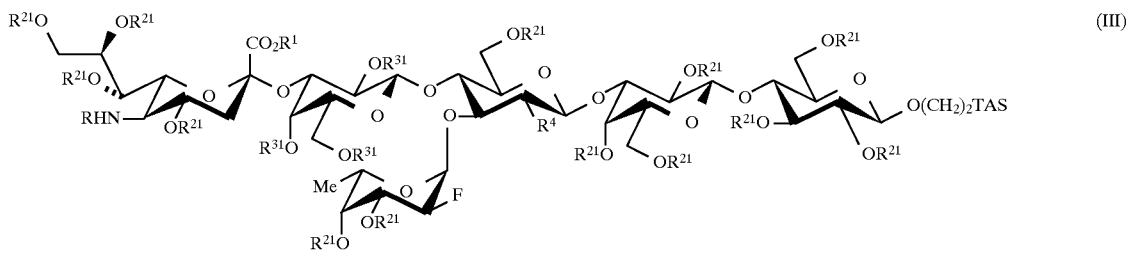

wherein R, $R^1$, $R^4$ and Me are as defined above; $R^{21}$ and $R^{31}$ independently denote a hydrogen atom, an unsubstituted or substituted phenylmethyl group having 7 to 13 carbon atoms, an aliphatic acyl group having 2 to 6 carbon atoms, or an aromatic acyl group having 7 to 13 carbon atoms; and TAS denotes a trialkylsilyl in which the alkyl group has 1 to 7 carbon atoms, provided that when $R^1$ is a hydrogen atom, $R^{21}$ and $R^{31}$ both denote a hydrogen atom; and $R^4$ denotes a hydroxy group, or an aliphatic or aromatic acylamino group; or when $R^1$ is a lower alkyl group, $R^{21}$ and $R^{31}$ denote an unsubstituted or substituted phenylmethyl group, or an aliphatic or aromatic acyl group; and $R^4$ denotes an aliphatic or aromatic acylamino group, or an aliphatic or aromatic acyloxy group.

Further, the present invention also relates to a compound represented by the general formula (IV):

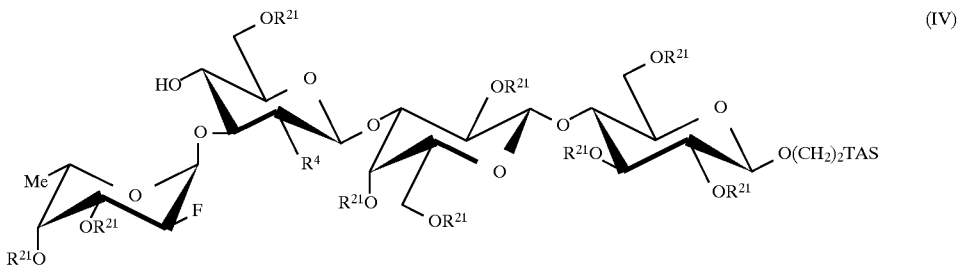

(IV)

wherein $R^{21}$, $R^4$ and TAS are as defined above, provided that when $R^{21}$ is a hydrogen atom, $R^4$ denotes a hydroxy group, or an aliphatic or aromatic acylamino group; or when $R^{21}$ is an aliphatic or aromatic acyl group, or an unsubstituted or substituted phenylmethyl group, $R^4$ denotes an aliphatic or aromatic acylamino group, or an aliphatic or aromatic acyloxy group.

The present invention further relates to a compound represented by the general formula (V):

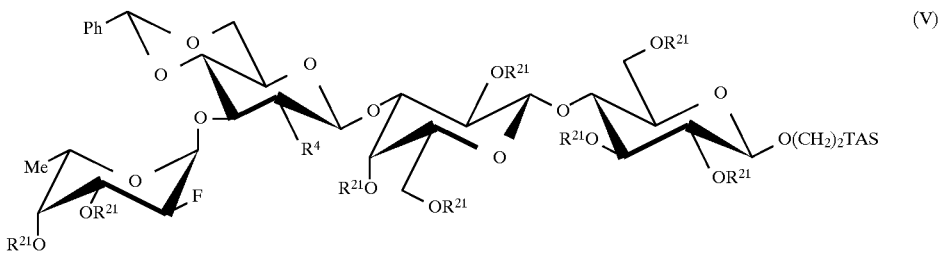

(V)

wherein $R^{21}$, $R^4$ and TAS are as defined above and Ph denotes an unsubstituted or substituted phenyl group, provided that when $R^{21}$ is a hydrogen atom, $R^4$ denotes a hydroxy group, or an aliphatic or aromatic acylamino group; or when $R^{21}$ is an unsubstituted or substituted phenylmethyl group, or an aliphatic or aromatic acyl group, $R^4$ denotes an aliphatic or aromatic acylamino group, or an aliphatic or aromatic acyloxy group, which compound is a precursor of the compound represented by the general formula (IV).

The present invention still further relates to a compound represented by the general formula (VI):

(VI)

wherein $R^6$ denotes an unsubstituted or substituted phenylmethyl group; and $R^9$ denotes a lower alkyl group having 1 to 5 carbon atoms, or an unsubstituted or substituted phenyl group having 6 to 12 carbon atoms.

The present invention also relates to a compound represented by the general formula (VII):

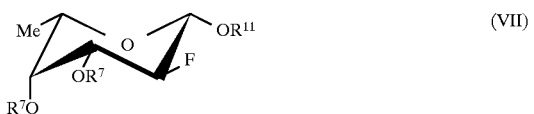

(VII)

wherein $R^{11}$ denotes a lower substituted alkyl group having 1 to 10 carbon atoms, or an unsubstituted or substituted phenylmethyl group having 7 to 13 carbon atoms; and $R^7$ denotes a hydrogen atom, an unsubstituted or substituted phenylmethyl group, an aliphatic acyl group having 2 to 6 carbon atoms or an aromatic acyl group having 7 to 13 carbon atoms.

The present invention also relates to a compound represented by the general formula (VIII):

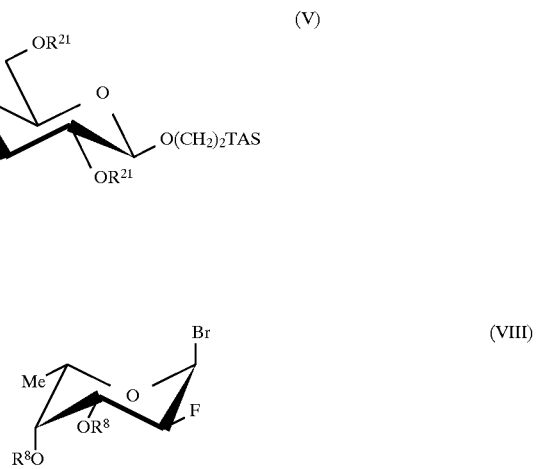

(VIII)

wherein $R^8$ denotes an aliphatic acyl group having 2 to 6 carbon atoms or an aromatic acyl group having 7 to 13 carbon atoms.

PREFERRED EMBODIMENTS OF THE INVENTION

Methods for preparing the sialyl Lewis X derivatives of the present invention will be illustratively described hereinafter.

As seen from the chemical structural formula (I-1), the fluorine substituted sialyl Lewis X derivative of the present invention is composed of a sialylgalactose moiety, a fucose moiety, a glucosamine lactose moiety and a ceramide moiety.

At first, the fucose moiety of the fluorine substituted sialyl Lewis X derivative is synthesized according to the following Reaction Scheme 1:

Reaction Scheme 1

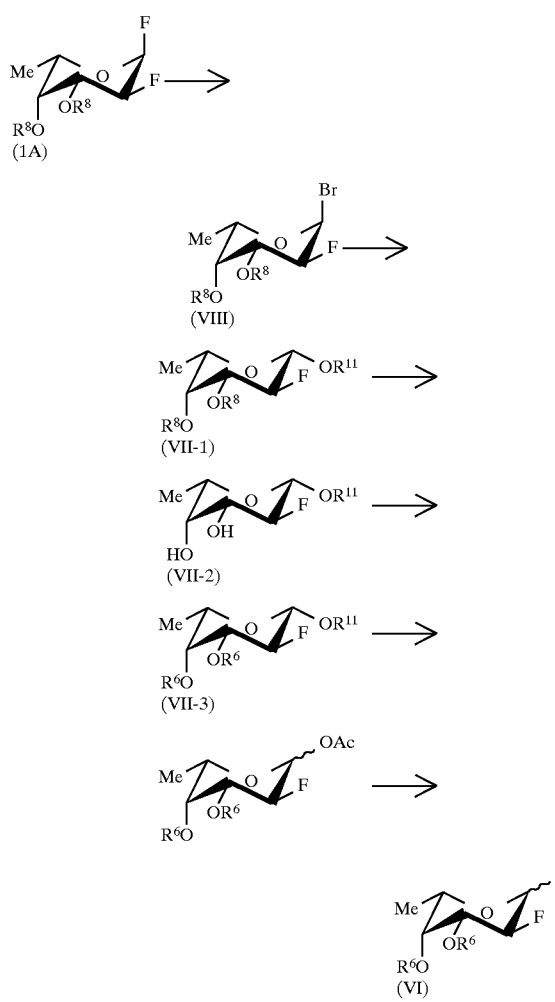

In the formulae, wherein $R^8$ denotes an aliphatic or aromatic acyl group; $R^{11}$ denotes a lower substituted alkyl group, or an unsubstituted or substituted phenylmethyl group; $R^6$ denotes an unsubstituted or substituted phenylmethyl group; and $R^9$ denotes a lower alkyl group, or an unsubstituted or substituted phenyl group.

Thus, a starting material, 3,4-di-O-acyl-2-deoxy-2-fluoro-α-L-fucopyranosyl fluoride (Compound 1A) is treated with a reagent such as hydrogen bromide/acetic acid, or phosphorus tribromide or phosphorous pentabromide, resulting in the formation of a compound of the general formula (VIII) in which the 1 position is brominated.

Compound 1A may be synthesized from L-fucopyranose tetracetate according to the method as described in Tetrahedron, 35, 2551–2554 (1979). Examples of $R^8$ include acetyl, propionyl, pivaloyl, sec-butyroyl, benzoyl, chlorobenzoyl and methoxybenzoyl. Introduction of such group in Compound 1A instead of acetyl group may be previously done in a conventional manner when synthesizing Compound 1A.

A compound of the general formula (VIII) may then be reacted with a lower substituted alcohol, benzyl alcohol or substituted phenylmethyl alcohol in the presence of, e.g., a silver salt to give a compound of the general formula (VII-1). Lower substituted alcohols used include trialkylsilylethyl alcohols in which the alkyl group may be methyl, ethyl, propyl, butyl, pentyl, hexyl, heptyl, octyl, nonanyl or decanyl, and 4-pentenylalcohol. Substituted phenylmethyl alcohols include 4-methoxybenzyl alcohol, 4-acetamidebenzyl alcohol, 4-nitrobenzyl alcohol, 4-chlorobenzyl alcohol or 4-bromobenzyl alcohol.

Then, the acyl type protective groups of the compound of the general formula (VII-1) are converted into benzyl type protective groups. Thus, the treatment of the compound of the general formula (VII-1) with sodium methoxide in methanol or sodium ethoxide in ethanol removes the acyl type protective group resulting in a compound of the general formula (VII-2), which is then protected with a desired protective group to give a compound of the general formula (VII-3).

Thus, a compound of the general formula (VII-2) is reacted with a benzyl halide or substituted phenylmethyl halide in the presence of a base such as sodium hydride, triethylamine, or an unsubstituted or substituted pyridine to convert into an unsubstituted or substituted phenylmethyl ether. The substituted phenylmethyls include 4-methoxybenzyl, 4-acetamidebenzyl, 4-nitrobenzyl, 4-chlorobenzyl and 4-bromobenzyl.

The —$OR^{11}$ group in the compound of the general formula (VII-3) is then converted through an acetyl (—OAc) group into a $SR^9$ group. For instance, when $R^{11}$ is a trialkylsilylethyl group, acetylation of the compound of the general formula (VII-3) is carried out with acetic anhydride in the presence of a Lewis acid such as boron trifluoride-ether complex, followed by treatment with an alkylthioating agent such as an alkylmercaptan or (alkylthio)trimethylsilane, or an unsubstituted or substituted thiophenol to give a compound of the general formula (VI).

When $R^{11}$ is an unsubstituted or substituted phenylmethyl group, for example, 4-methoxybenzyl group, the compound of the general formula (VI) is prepared by selectively removing the protective group at the 1 position by means of DDQ (2,3-dichloro-5,6-dicyano-1,4-benzoquinone), followed by acetylation with acetic anhydride, and treatment with an alkylthioating agent such as an alkylmercaptan or (alkylthio)trimethylsilane, or an unsubstituted or substituted thiophenol.

A preferred embodiment for precontaining fucose containing fucose derivative of the general formula (VI) is shown in the following Reaction Scheme 2:

Reaction Scheme 2

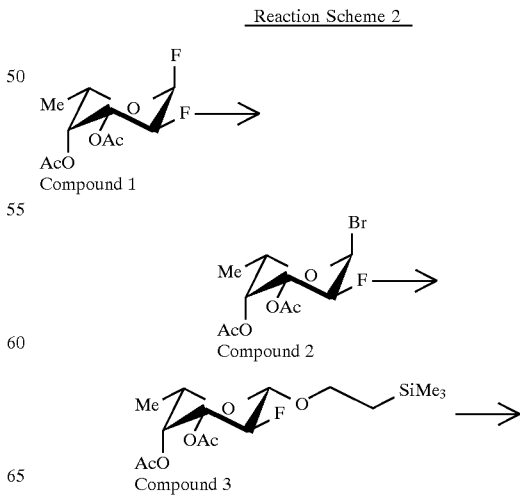

-continued
Reaction Scheme 2

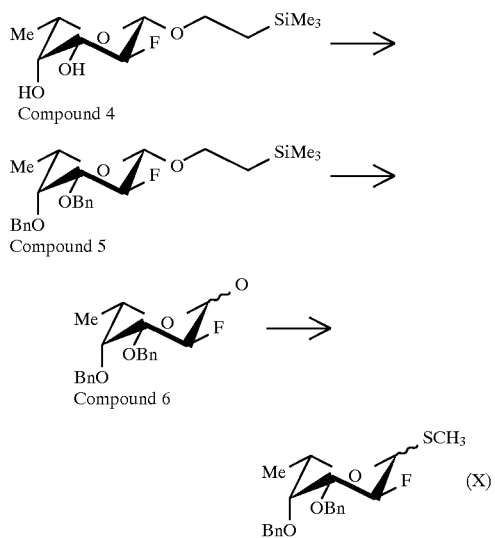

In the formulae, Me denotes a methyl group, Ac denotes an acetyl group, and Bn denotes a benzyl group.

The starting material, 3,4-di-O-acetyl-2-deoxy-2-fluoro-α-L-fucopyranosyl fluoride (Compound 1) is treated with hydrogen bromide/acetic acid to convert it into Compound 2 in which the 1 position is brominated. Compound 2 is reacted with trimethylsilyl ethanol in the presence of a silver salt to yield Compound 3. Compound 3 is deprotected to yield Compound 4, from which Compound 5 is then derived. Compound 5 is further reacted with acetic anhydride at −30 to 0° C. for 3 hours in the presence boron trifluoride-ether complex to yield Compound 6. Compound (X) included in the general formula (VI) is obtained by reacting Compound 6 with boron trifluoride-ether complex and (methylthio)trimethylsilane.

As shown in Reaction Scheme 3, the thus obtained fucose derivative of the general formula (VI) is condensed with a glucosamine lactose derivative (Compound 7) to obtain a condensed compound. The condensed compound is reduced to a compound of the general formula (IV-1) optionally after changing protective groups for hydrogen groups. The reduced compound is then condensed with a sialyl galactose derivative of the general formula (XIII) to give a compound of the general formula (III-1).

Compound 7 and the compound of the general formula (XIII) may easily be synthesized according to a method similar to that described in Carbohydrate Research, 200, 269–285 (1990).

Reaction Scheme 3

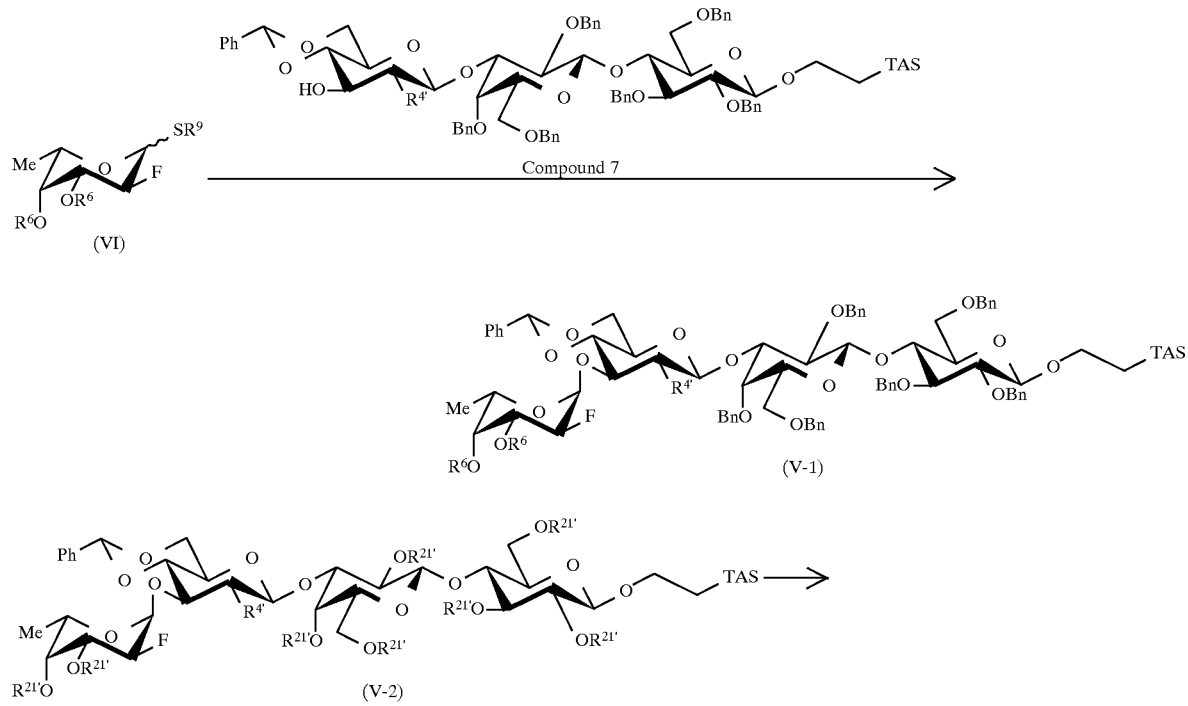

-continued
Reaction Scheme 3

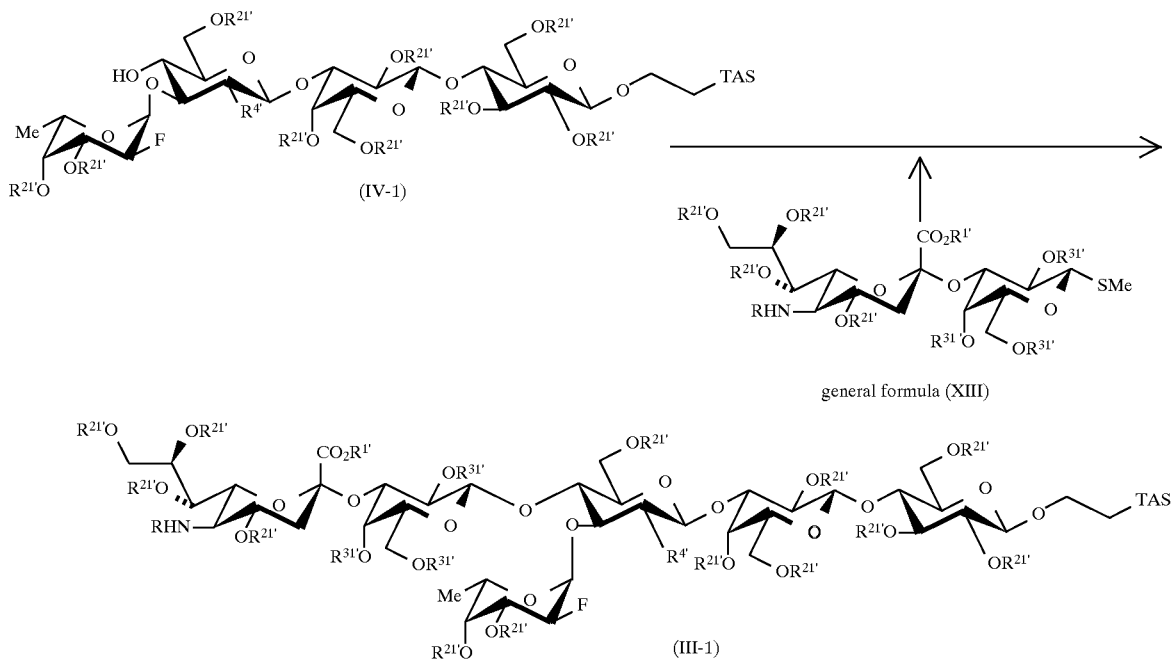

general formula (XIII)

In the above formulae, TAS denotes a trialkylsilyl group; Ph denotes an unsubstituted or substituted phenyl group; $R^{4'}$ denotes an aliphatic or aromatic acyloxy group, or an aliphatic or aromatic acylamino group; $R^{21'}$ and $R^{31'}$ independently denote an unsubstituted or substituted phenylmethyl group, or an aliphatic or aromatic acyl group; R denotes an aliphatic acyl group; $R^{1'}$ denotes a lower alkyl group; and $R^6$, $R^9$, Me and Bn are as defined above.

A compound of the general formula (VI) is condensed with Compound 7 in an inert solvent such as benzene, toluene, methylene chloride or mixture thereof in the presence of an appropriate glycosylation accelerator such as N-iodosuccinimide/tetrabutyl ammonium triflate, or dimethyl(methylthio)sulfonium triflate, or N-bromosuccinimide/silver trifluoromethanesulfonate to give a compound of the general formula (V-1).

Compound 7 may be easily synthesized according to a method similar to that described in Carbohydrate Research, 200, 269–285 (1990).

The protective groups for hydroxy groups in the resultant compound of the general formula (V-1) may be changed to other desired protective groups. For example, the compound (V-1) may be subjected to catalytic reduction under hydrogen atmosphere to remove the protective groups for hydroxy groups to replace them by hydrogen atoms. A substituted phenylmethyl group different from the removed protective group, such as 4-methoxybenzyl, 4-acetamidebenzyl, 4-nitrobenzyl, 4-chlorobenzyl or 4-bromobenzyl, can be introduced in the presence of a base such as sodium hydride, triethylamine, or an unsubstituted or substituted pyridine. Alternatively, after the hydroxy-protective groups are replaced with hydrogen atoms as described above, an aliphatic or aromatic acyl group, such as acetyl, propionyl, pivaloyl, sec-butyroyl, benzoyl, chlorobenzoyl or 4-methoxybenzoyl, may be introduced by the reaction with an acylating agent such as an acyl halide or acid anhydride in the presence of a base such as sodium hydride, triethylamine, or an unsubstituted or substituted pyridine. The alkyl groups in the trialkylsilyl group may be identical with or different from each other and include methyl, ethyl, propyl, butyl, pentyl, hexyl, heptyl, octyl, nonanyl or decanyl. Thus, a compound of the general formula (V) is obtained.

Then, the cyclic benzylidene moiety in the compound of the general formula (V-2) is reduced with a metal hydride such as sodium borohydride, sodium cyanoborohydride, lithium aluminium hydride, borane-trimethylamine or triethylsilane in an inert solvent such as tetrahydrofuran or ether to give a compound of the general formula (IV-1).

The group $R^{21'}$ in the compound of the general formula IV-1 can be removed. When $R^{21'}$ is an aliphatic or aromatic acyl group, it may be replaced with a hydrogen atom by treating the compound with sodium methoxide in methanol or sodium ethoxide in ethanol. When $R^{21'}$ is an unsubstituted or substituted phenylmethyl group, it may be removed by catalytic reduction of the compound under hydrogen atmosphere. When $R^{4'}$ is an aliphatic or aromatic acyloxy group, it may be converted into a hydroxy group by treating the compound with sodium methoxide in methanol or sodium ethoxide in ethanol. Thus, a compound of the general formula (IV) may be obtained.

A compound of the general formula (IV-1) is condensed with a compound of the general formula (XIII) to give a compound of the general formula (III-1). That is, a compound of the general formula (IV-1) is condensed with a compound of the general formula (XIII) in an inert solvent such as benzene, toluene, methylene chloride or mixture thereof in the presence of an appropriate glycosylation promotor such as N-iodosuccinimide/tetrabutyl ammonium triflate, dimethyl(methylthio)sulfonium triflate, or N-bromosuccinimide/silver trifluoromethanesulfonate to give a compound of the general formula (III-1).

The compound of the general formula (XIII) ma y be easily synthesized according to a meth of similar to that described in Carbohydrate Research, 200, 269–285 (1990).

When in the compound of the general formula (III-1) $R^1$ is a lower alkyl group, $R^{21'}$ and $R^{31'}$ are aliphatic or aromatic acyl groups, and $R^{4'}$ is an aliphatic or aromatic acyloxy group, these protective groups can be converted to hydrogen atoms by the treatment of the compound with sodium methoxide in methanol or sodium ethoxide in ethanol. When $R^{21'}$ and $R^{31'}$ is unsubstituted or substituted phenylmethyl groups, $R^1$ is a lower alkyl group, and $R^4$ is an aliphatic or aromatic acylamino group, $R^{21}$ and $R^{31}$ can be removed by catalytic reduction of the compound under hydrogen atmosphere. Further, an aliphatic or aromatic acyl group, such as acetyl, propionyl, pivaloyl, sec-butyloyl, benzoyl, chlorobenzoyl or methoxybenzoyl, may be introduced by the reaction with an acylating agent such as an acyl halide or acid anhydride in the presence of a base such as sodium hydride, triethylamine or an unsubstituted or substituted pyridine. Thus, a compound of the general formula (III) is obtained.

A preferred embodiment of for preparing a compound of the general formula (III) is shown in the following Reaction Scheme 4.

As shown in Scheme 4, the thiomethyl compound (X) is reacted with Compound 7 in an inert solvent such as benzene, toluene, methylene chloride or mixture thereof in the presence of an appropriate glycosylation promotor, such as N-iodosuccinimide/tetrabutylammonium triflate or dimethyl(methylthio)sulfonium triflate at 0° C. for 2 to 3 hours to give Compound 8. The reduction of the benzylidene moiety in glucosamine of the compound results in Compound 9. The reduction may be completed with the use of an appropriate reducing agent such as sodium boron hydrocyanide, borane-trimethylamine or triethylsilane in an inert solvent such as tetrahydrofuran or ether at 0° to 30° C. within 2 hours. Compound 9, whose hydroxy groups are all protected except the hydroxy group at the 4 position of the glucosamine moiety, is linked to a sialylgalactose (Compound 10) to give Compound 11.

As shown in Reaction Scheme 5, a trialkylsilylethyl group is removed from the compound of the general formula (III-1) (when the compound has benzyl type protective groups, they should be converted into acyl type protective groups) to give a detrialkylsilylethylated compound. The

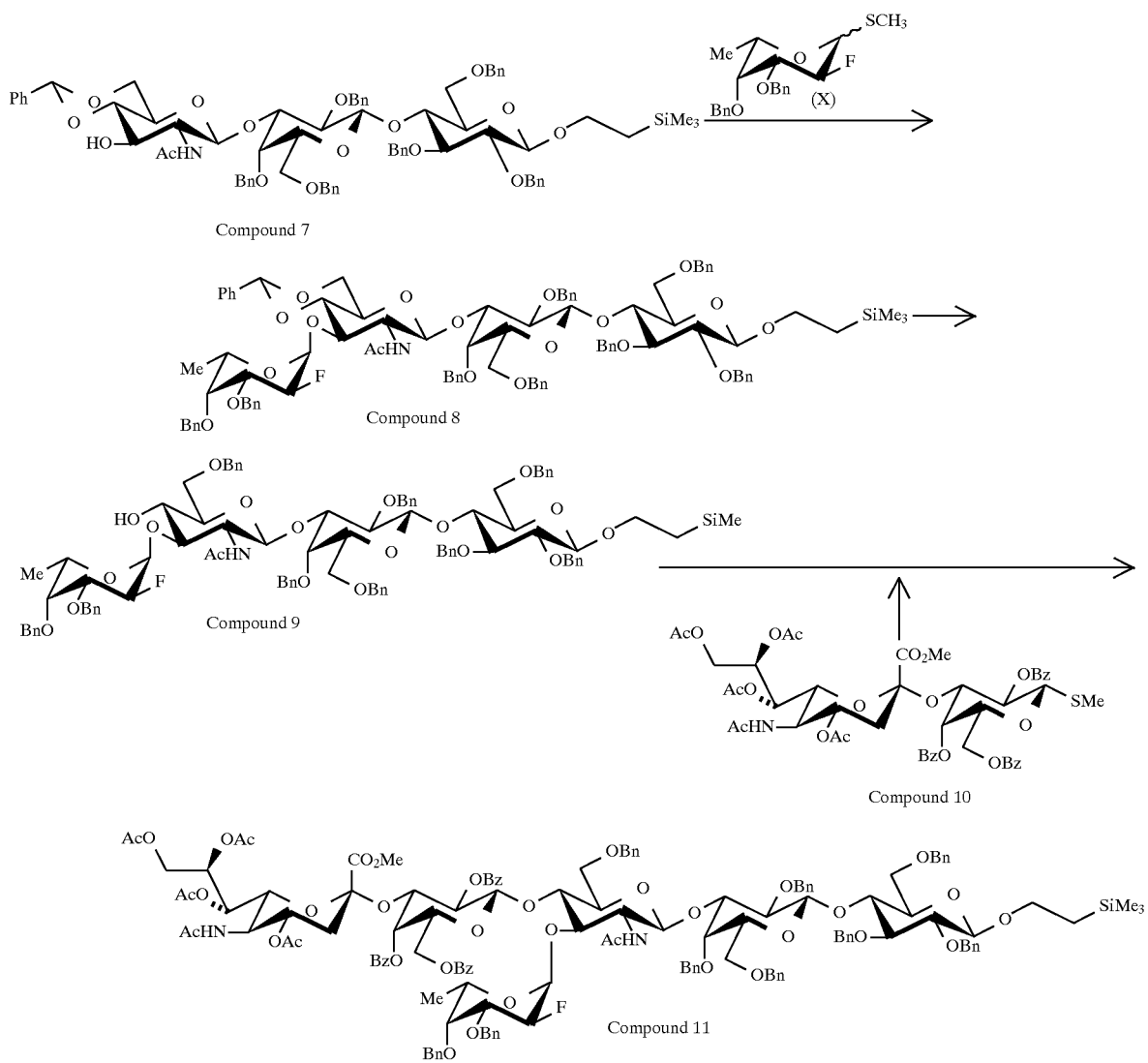

compound is activated to obtain a compound, which is then condensed with a sphingosine derivative of the general formula (XIV) to yield a compound of the general formula (I-21).

converted into a fluorine atom, a thioalkyl group, a thioaryl group, or trichloroacetoimidate [—OC(NH)CCl$_3$], respectively.

Reaction Scheme 5

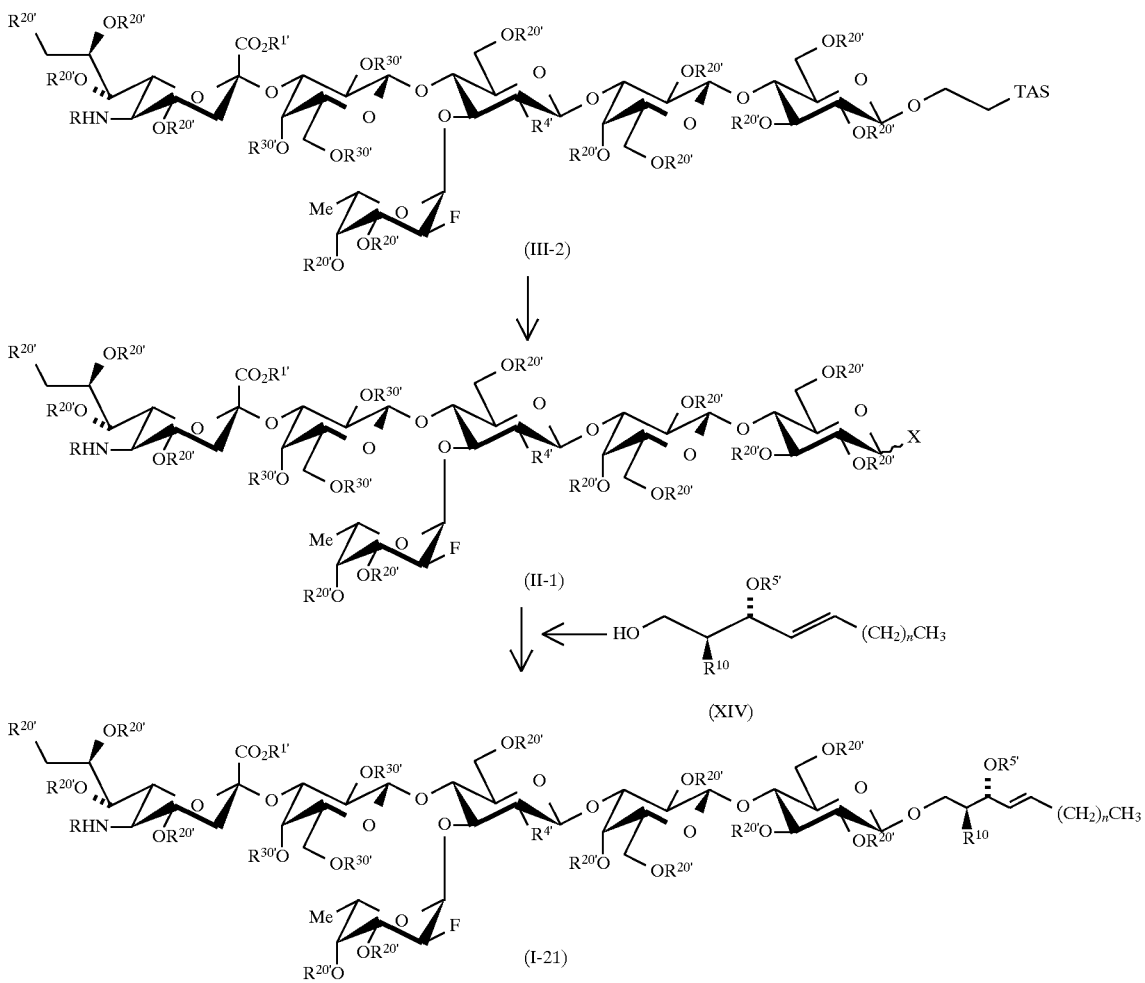

In the formulae, $R^{20'}$, $R^{30'}$ and $R^{5'}$ denote aliphatic or aromatic acyl groups; $R^{12}$ denotes $N_3$, $NH_2$ or $NHCORa$ group in which Ra denotes a saturated or unsaturated alkyl group; n denotes an integer of 0 to 20; X denotes a hydroxy group, a fluorine atom, a thioalkyl group, a thioaryl group or —OC(NH)CCl$_3$ group; and R, $R^{1'}$, $R^{4'}$ and TAS are as defined above.

Removal of the trialkylsilylethyl group is carried out by treating a compound of the general formula (III-2) with a Lewis acid, such as trifluoroacetic acid or boron trifluoride-ether complex.

The thus obtained compound of the general formula (II-1) wherein X is a hydroxy group may be subjected to treatment with diethylaminosulfur trifluoride (DAST), acetylation with acetic anhydride followed by treatment with an alkylthiotrimethylsilane in the presence of a Lewis acid, acetylation with acetic anhydride followed by treatment with an aromatic mercaptan in the presence of a Lewis acid, or treatment with trichloroacetonitrile (CCl$_3$CN) in the presence of 1,8-diazabicyclo[5.4.0]undeca-7-ene (DBU) to yield a compound of the general formula (II-1) in which X is Finally, a compound of the general formula (II-1) is condensed with a sphingosine derivative of the general formula (XIV) in the presence of various glycosylation promotor such as boron trifluoride-ether complex, trialkylsilyl trifluoromethanesulfonate, N-iodosuccinimide/tetrabutylammonium triflate, dimethyl(methylthio) sulfonium triflate, tin (II) chloride/silver perchlorate or zirconocene/silver trifluoromethanesulfonate to yield a compound of the general formula (I-21).

The compound of the general formula (XIV) can be easily obtained by synthesizing azide sphingosine according to the method described in Carbohydrate Research, 202, 177–191 (1990), protecting a primary hydroxy group at the 1 position with an appropriate protective group such as triphenylmethyl group, protecting a hydroxy group at the 3 position in a conventional manner using, e.g. benzoyl chloride, and deprotecting the position 1 by means of, e.g. boron trifluoride-ether complex.

As shown in Scheme 6, when $R^{10}$ in the sphingosine moiety of the compound of the general formula (I-21) is an azide group, the azide group can be selectively reduced (for example, with hydrogen sulfide) and the reduced compound is reacted with a desired carboxylic acid in the presence of a dehydrating condensation agent such as 1,2-dicyclohexylcarbodiimide (DCC) or 1-ethyl-3-(3-dimethylaminopropyl)carbodiimide (WSC) to obtain a fully-protected, fluorine substituted sialyl Lewis X ganglioside (I-11).

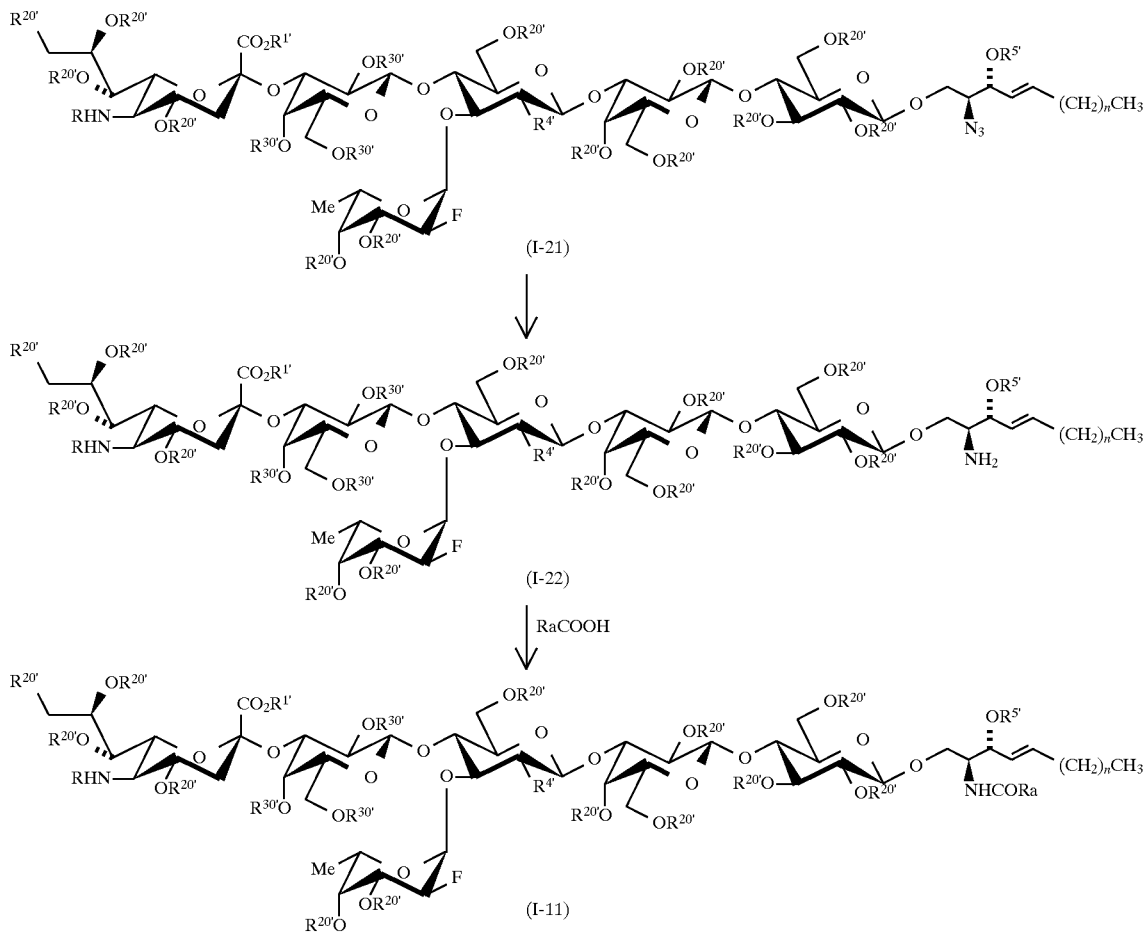

In the formulae, Ra denotes a saturated or unsaturated aliphatic group; and R, $R^{1'}$, $R^{20'}$, $R^{30'}$, $R^{4'}$, $R^{5'}$ and n are as defined above.

De-O-acylation under alkaline conditions such as sodium methoxide-methanol or sodium ethoxide-ethanol and hydrolysis of $COOR^{1'}$ group may yield a fluorine substituted sialyl Lewis X ganglioside of the general formula (IX), i.e., a compound of the general formula (I-1) in which $R^1$, $R^{20}$, $R^{30}$ and $R^5$ are hydrogen atoms and $R^4$ is a hydroxy or acetylamino group.

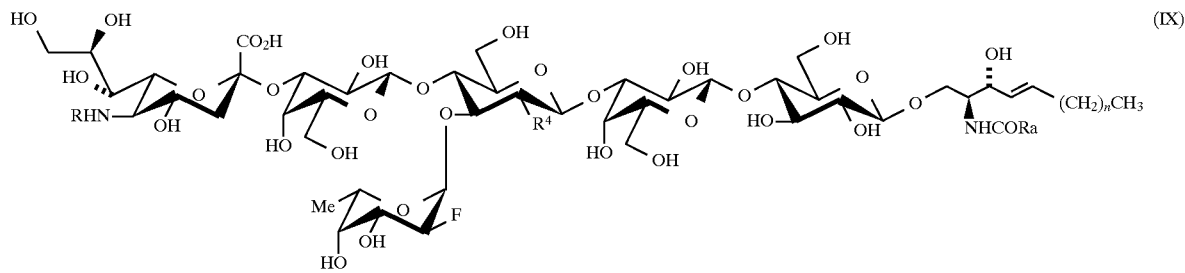

A preferred embodiment is shown in the following Reaction Scheme 7.

Reaction Scheme 6
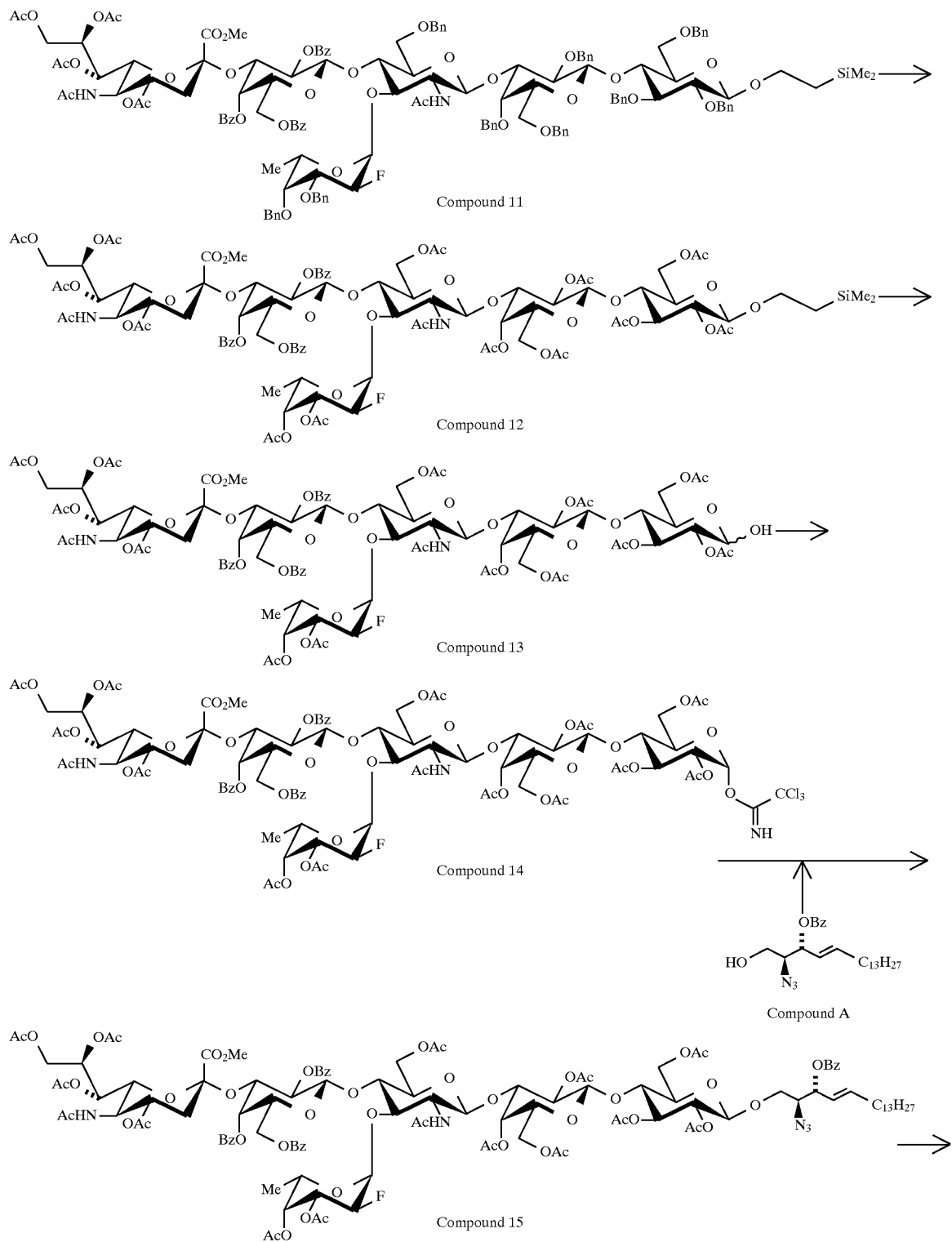

-continued
Reaction Scheme 6

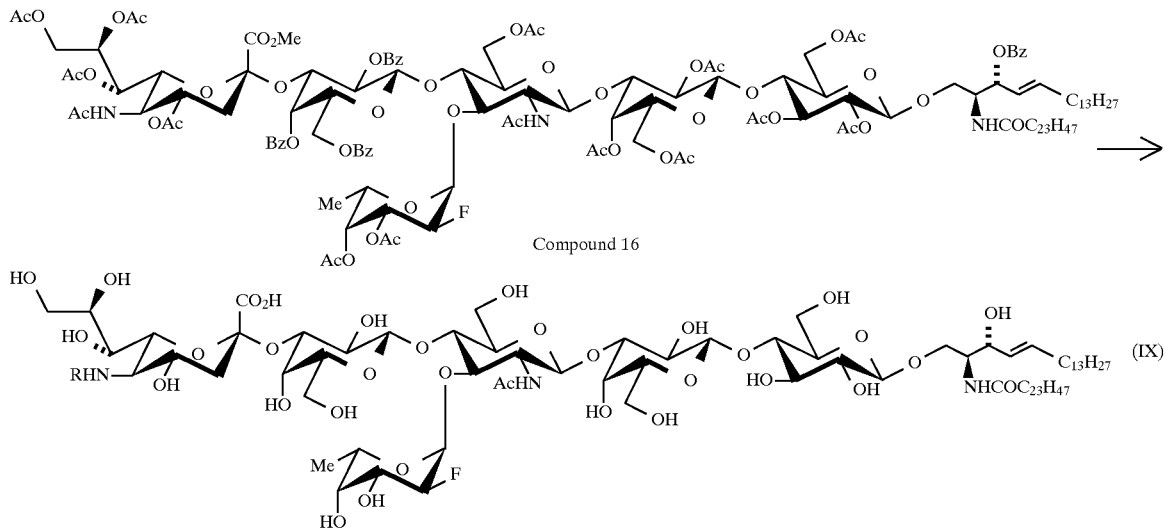

Compound 16

(IX)

The benzyl group of Compound 11 is removed by catalytic reduction and the resulting free hydroxy group is acetylated to yield Compound 12 included in the general formula (II). The removal of trimethylsilylethyl group at the 2 position of glucose in Compound 12 by the action of trifluoroacetic acid gives Compound 13 included in the general formula (II). Compound 13 is treated with 1,8-diazabicyclo[5.4.0]undeca-7-ene (DBU) and trichloroacetonitrile ($CCl_3CN$) to yiled Compound 14 included in the general formula (II). Then, Compound 14 is treated with boron trifluoride ether complex in the presence of the azide sphingosine derivative (Compound A) to give Compound 15 included in the general formula (I). The azide group of Compound 15 is then reduced with hydrogen sulfide gas followed by condensation with tetracosanoic acid in the presence of a dehydrating condensation agent such as 1-ethyl-3-(3-dimethylaminopropyl)carbodiimide hydrochloride to give Compound 16. Compound 16 is then deprotected to give the desired fluorine substituted sialyl Lewis X derivative, Compound (IX). The reducing agent used to reduce said azide group is not limited to hydrogen sulfide, but includes any reducing agent which can reduce an azide group, does not reduce a double bond and does not release an acyl protective group. This reaction process is as shown in Reaction Scheme 3.

The compounds of the present invention are expected to have selectin adhesion inhibiting activity and metabolic stability and, accordingly, to be capable of inhibiting neutrophils (one kind of leucocytes)-dependent and selectin-dependent acute inflammation and to be useful for the treatment and prevention of inflammation, and thrombopoiesis associated with inflammation, asthma, rheumatism, immunological diseases and cancers.

The present invention will be described by way of examples but is never limited thereto.

EXAMPLES

Example 1

Synthesis of 3,4-di-O-acetyl-2-deoxy-2-fluoro-α-L-fucopyranosyl bromide (referred to as Compound 2 hereinafter).

Compound 1 (0.300 g, 1.19 mmol) was dissolved in 0.7 ml of a mixed solvent of acetic acid:acetic anhydride (2:1).

The solution was cooled with ice-water, and 1.35 ml (281 mmol) of a 33% solution of hydrogen bromide and acetic acid (Merck) was added thereto at 10° C. The reaction mixture was sealed, removed from the ice bath and stirred at an internal temperature of 20° to 25° C. for 24 hours. The reaction mixture was diluted with dichloromethane and washed with cooling water, a saturated aqueous sodium bicarbonate, and cooling water, successively. After drying over sodium sulfate, vacuum concentration gave 0.364 g (yield: 97.7%) of Compound 2.

$C_{10}H_{14}O_5BrF$ (313.12)

$^1$H-NMR ($CDCl_3$; TMS): δ6.61 (d, 1H, $J_{1,2}$=4.2 Hz, H-1), 5.48 (dd, 1H, $J_{2,3}$=10.0 Hz, 1H, $J_{3,4}$=3.4 Hz, H-3), 5.38 (dd, 1H, $J_{3,4}$=3.4 Hz, $J_{4,5}$=1.0 Hz, H-4), 4.74 (ddd, 1H, $J_{F,2}$=50.5 Hz, $J_{1,2}$=4.2 Hz, $J_{2,3}$=10.0 Hz, H-2), 4.44 (m, 1H, H-5), 2.17, 2.07 (2s, 6H, 2AcO), 1.22 (d, 3H, $J_{5,6}$=6.5 Hz, H-6).

$^{19}$F-NMR ($CDCl_3$; $CFCl_3$): δ-195 (ddd, $J_{F,2H}$=50.5 Hz, $J_{F,3H}$=9.4 Hz, $J_{F,1H}$=3.0 Hz)

Example 2

Synthesis of 2-(trimethylsilyl)ethyl 3,4-di-O-acetyl-2-deoxy-2-fluoro-β-L-fucopyranoside (referred to as Compound 3 hereinafter).

Compound 2 (0.364 g, 1.16 mmol) was dissolved in 2 ml of anhydrous dichloromethane and 180 mg of activated Molecular Sieve 4 Å was added thereto. The mixture was stirred under argon atmosphere for 1 hour (Mixture A). On the other hand, 0.16 ml (1.12 mmol) of 2-(trimethylsilyl) ethanol, 0.130 g (0.63 mmol) of silver perchlorate and 0.170 g (0.62 mmol) of silver carbonate were mixed with 1 ml of anhydrous dichloromethane under argon atmosphere, and 180 mg of activated Molecular Sieve 4 Å was added to the mixture followed by stirring it at room temperature for 2 hours while shielding from light (Mixture B). Both mixtures were cooled with ice, and Mixture A was added to Mixture B. The resulting mixture was heated to room temperature while shielding from light and stirred for 12 hours. Insoluble materials were filtered out and washed with dichloromethane. The filtrate and washing liquids were combined, washed with 5% aqueous sodium carbonate solution and dried over sodium sulfate. After vacuum concentration of solvents, the residue was subjected to flash chromatography with an eluent of n-hexane:ethyl acetate (6:1) to give Compound 3 (277 mg, 68.0%).

$C_{15}H_{27}O_6FSi$ (350.47)

melting point: 48°–50° C.

$[\alpha]_D^{24} = -26.4°$ (c 1.0, $CHCl_3$)

$IR^{KBr}_{max}$ cm$^{-1}$: 1750, 1270 (ester), 870, 840 ($Me_3Si$), $^1$H-NMR ($CDCl_3$; TMS): $\delta$5.26 (ddd, 1H, $J_{3,4}=J_{F,4}$=2.7 Hz, $J_{4,5}$=1.0 Hz, H-4), 5.09 (ddd, 1H, $J_{F,3}$=14 Hz, $J_{2,3}$=9.7 Hz, $J_{3,4}$=2.7 Hz, H-3), 4.53 (d, 1H, $J_{1,2}$=7.7 Hz, H-1), 4.45 (ddd, 1H, $J_{F,2}$=44 Hz, $J_{2,3}$=9.7 Hz, $J_{1,2}$=7.7 Hz, H-2), 4.03 (m, 1H, CHCH$_2$Si), 3.82 (dq, 1H, $J_{5,6}$=6.5 Hz, $J_{4,5}$=1.0 Hz, H-5), 3.60 (m, 1H, CHCH$_2$Si), 2.05, 2.15 (s, 6H, 2AcO), 1.21 (d, 3H, $J_{5,6}$=6.5 Hz, H-6), 1.04 (m, 2H, CH$_2$CH$_2$SiMe$_3$).

$^{19}$F-NMR ($CDCl_3$; $CFCl_3$): $\delta$–207 (dd, 1F, $J_{F,2H}$=44 Hz, $J_{F,3H}$=14 Hz, 2-F), Mass spectrometry: m/z calculated for $C_{15}H_{27}O_6FSi$ 351.1639 (M+H); found 351.1637.

Example 3

Synthesis of 2-(trimethylsily)ethyl 3,4-di-O-benzyl-2-deoxy-2-fluoro-β-L-fucopyranoside (referred to as Compound 5 hereinafter).

Compound 3 (0.277 g, 0.79 mmol) was dissolved in 1.5 ml of absolute methanol and 8 mg (0.15 mmol) of sodium methoxide was added followed by stirring the reaction solution at room temperature for 2.5 hours under argon atmosphere. The reaction solution as such was adsorbed on Anberlite IR-120 (H Type). Elution was effected with methanol and the eluate was filtered. The filtrate was concentrated under vacuum and the residue (0.187 g) was dissolved in 4 ml of anhydrous dimethylformamide. Under argon atmosphere, 60 mg (1.5 mmol) of oily sodium hydride (about 60%) was added at 0° C. The mixture was stirred at the same temperature for 30 minutes and 0.26 ml (2.2 mmol) of benzyl bromide was dropwise added thereto at the same temperature. The mixture was reacted under stirring at 0° C. for 30 minutes, heated to room temperature and stirred for 2 hours. The reaction mixture was again cooled to 0° C. and 0.15 ml of methanol was added followed by vacuum concentration and vacuum drying. The residue was subjected to flash chromatography with an eluent of n-hexane:ethyl acetate (8:1) to give Compound 5 (339 mg, 96.0%).

$C_{25}H_{35}O_4FSi$ (446.65)

$[\alpha]_D^{25}=+19.4°$ (c 1.0, $CHCl_3$)

$IR^{neat}_{max}$ cm$^{-1}$: 1120 (ether), 860, 840 ($Me_3Si$), 700 (Ph).

$^1$H-NMR ($CDCl_3$; TMS): $\delta$7.26–7.40 (m, 10H, Ph), 4.81 (ABq, 2H, CH$_2$Ph), 4.74 (ABq, 2H, CH$_2$Ph), 4.69 (ddd, 1H, $J_{F,2}$=51 Hz, $J_{1,2}=J_{2,3}$=7.6 Hz, H-2), 4.38 (dd, $J_{1,2}$=7.6 Hz, $J_{F,1}$=4.3 Hz, H-1), 4.00 (m, 1H, CHCH$_2$Si), 3.55 (m, 1H, CHCH$_2$Si), 3.65–3.55 (m, 2H, H-4, H-3), 3.48 (q, 1H, $J_{5,6}$=6.5 Hz, H-5), 1.19 (d, 3H, $J_{5,6}$=6.5 Hz, H-6), 1.04 (m, 2H, CH$_2$CH$_2$SiMe$_3$).

$^{19}$F-NMR ($CDCl_3$; $CFCl_3$): $\delta$–206 (dd, 1$_F$, $J_{F,2H}$=51 Hz, $J_{F,3H}$=12 Hz, 2-F).

Mass spectrometry: m/z calculated for $C_{25}H_{35}O_4FSi$ 447.2366 (M+H); found 447.2356.

Example 4

Synthesis of 1-O-acetyl-3,4-di-O-benzyl-2-deoxy-2-fluoro-α,β-L-fucopyranose (referred to as Compound 6 hereinafter).

Compound 5 (0.220 g, 0.493 mmol) was dissolved in 4 ml of anhydrous toluene and 0.7 ml of acetic anhydride. The solution was cooled to –30° C. under argon atmosphere, and 50 μl (0.41 mmol) of boron trifluoride-ether complex was dropwise added thereto. While stirring, the reaction mixture was heated to 0° C. over 3 hours, diluted with dichloromethane and washed with 1M aqueous sodium carbonate solution and saturated sodium chloride aqueous solution. After drying over sodium sulfate and vacuum concentration, the residue was subjected to flash chromatography with an eluent of n-hexane:ethyl acetate (6:1) to give Compound 6 (α:β=1:2, 187 mg, 97.8%).

$C_{22}H_{25}O_5F$ (388.44)

$IR^{neat}_{max}$ cm$^{-1}$: 1730, 1250 (ester), 730, 700 (Ph).

$^1$H-NMR ($CDCl_3$; TMS): $\delta$ 7.2–7.5 (m, 10H, Ph), 6.38 (d, 0.33H, $J_{1,2}$=4.0 Hz, αH-1), 5.65 (dd, 0.66H, $J_{1,2}$=8.0 Hz, $J_{F,1H}$=4.8 Hz, βH-1), 2.14 (s, 0.66H, Ac (β)), 2.12 (s, 0.33H, Ac (α)), 1.19 (d, 2H, $J_{5,6}$=6.4 Hz, .βH-6), 1.16 (d, 1H, $J_{5,6}$=6.4 Hz, αH-6).

Example 5

Synthesis of methyl 3,4-di-O-benzyl-2-deoxy-2-fluoro-1-thio-α,β-L-fucopyranose (referred to as Compound X hereinafter).

Compound 6 (0.187 g, 0.481 mmol) was dissolved in 5 ml of anhydrous dichloromethane, and 0.33 ml (2.33 mmol) of (methylthio)trimethylsilane was added under argon atmosphere. The mixture was cooled to 0° C. and 0.13 ml (1.06 mmol) of boron trifluoride-ether complex was dropwise added thereto. The mixture was then heated to room temperature, stirred for 19 hours, diluted with dichloromethane, and washed with 1M aqueous sodium carbonate solution and saturated sodium chloride aqueous solution. After drying over sodium sulfate and concentrating under vacuum, the residue was subjected to flash chromatography with an eluent of n-hexane:ethyl acetate (8:1) to yield Compound X (α:β=3:2, 133 mg, 97.8%).

$C_{21}H_{25}O_3FS$ (376.50)

$IR^{neat}_{max}$ cm$^{-1}$: 1120 (ether), 730, 700 (Ph).

Mass spectrometry: m/z calculated for $C_{21}H_{25}O_3FS$ 377.1587 (M+H); found 377.1588.

α;$^1$H-NMR ($CDCl_3$; TMS): $\delta$ 7.5–7.2 (m, 10H, Ph), 5.42 (d, 1H, $J_{1,2}$=5.7 Hz, αH-1), 5.22 (ddd, 1H, $J_{F,2}$=50 Hz, $J_{2,3}$=10 Hz, $J_{1,2}$=5.7 Hz, H-2), 4.81 (ABq, 2H, CH$_2$Ph), 4.75 (ABq, 2H, CH$_2$Ph), 4.18 (dq, 1H, $J_{4,5}$=1.0 Hz, $J_{5,6}$=6.4 Hz, H-5), 3.86 (ddd, 1H, $J_{F,3}$=9.3 Hz, $J_{2,3}$=10 Hz, $J_{3,4}$=3.1 Hz, H-3), 3.68 (ddd, 1H, $J_{F,4}$=4.3 Hz, $J_{3,4}$=3.1 Hz, $J_{4,5}$=1.0 Hz, H-4), 2.10 (s, 3H, SCH$_3$), 1.17 (d, 3H, $J_{5,6}$=6.4 Hz, H-6).

$^{19}$F-NMR ($CDCl_3$; $CFCl_3$): $\delta$ –198 (ddd, 1F, $J_{F,2H}$=50 Hz, $J_{F,3}$=9.3 Hz, $J_{F,4H}$=4.3 Hz, 2-F), β;$^1$H-NMR ($CDCl_3$; TMS): $\delta$ 7.5–7.2 (m, 10 H, Ph), 4.82 (ABq, 2H, CH$_2$Ph), 4.76 (ABq, 2H, CH$_2$Ph), 4.76 (ddd, 1H, $J_{F,2}$=51 Hz, $J_{1,2}=J_{2,3}$=9.5 Hz, H-2), 4.34 (dd, 1H, $J_{1,2}$=9.5 Hz, $J_{F,1}$=3.2 Hz, H-1), 3.7–3.6 (m, 2H, H-3 and H-4), 3.55 (q, 1H, $J_{5,6}$=6.5 Hz, H-5), 2.21 (s, 3H, S-CH$_3$), 1.22 (d, 3H, $J_{5,6}$=6.5 Hz, H-6).

$^{19}$F-NMR ($CDCl_3$; $CFCl_3$): $\delta$ –197 (ddd, 1F, $J_{F,2H}$=51 Hz, $J_{F,3H}$=13.1 Hz, $J_{F,1H}$=3.2 Hz, 2-F).

Example 6

Synthesis of 2-(trimethylsilyl)ethyl O-(3,4-di-O-benzyl-2-deoxy-2-fluoro-α-L-fucopyranosyl)-(1→3)-O-(2-acetamide-4,6-O-benzylidene-2-deoxy-β-D-glucopyranosyl)-(1→3)-O-(2,4,6-tri-O-benzyl-β-D-galactopyranosyl)-(1→4)-2,3,6-tri-O-benzyl-β-D-glucopyranoside (referred to as Compound 8 hereinafter).

Compound X (90 mg, 0.239 mmol) and 2-(trimethylsilyl) ethyl O-(2-acetamide-4,6-O-benzylidene-2-deoxy-β-D- glucopyranosyl)-(1→3)-O-(2,4,6-tri-O-benzyl-δ-D-galactopyranosyl)-(1→4)-2,3,6-tri-O-benzyl-β-D-glucopyranoside (referred to as Compound 7 hereinafter). (220 mg, 0.173 mmol) were dissolved in 7 ml of anhydrous benzene, and 1 g of activated Molecular Sieve 4 Å was added under argon atmosphere. After stirring at room temperature for 8 hours, the reaction mixture was cooled to about 7° C. A mixture of 360 mg (1.39 mmol) of dimethyl (methylthio) sulfonium triflate and 360 mg of activated Melecular Sieve 4 Å was added thereto and the resulting reaction mixture was stirred at the same temperature for 1.5 hours. It was then cooled to 4° C., and 3.6 ml of methanol and then 1.2 ml of triethylamine were added thereto. The mixture was stirred at the same temperature for 30 minutes. Insoluble materials were suction filtrated out and washed with dichloromethane. The filtrate and washing liquids were combined, washed with water, dried over sodium sulfate, and vacuum concentrated. The residue was subjected to flash chromatography with an eluent of n-hexane-ethyl acetate (5:2) to yield Compound 8 (195 mg, 70.4%).

$C_{94}H_{108}NO_{19}FSi$ (1603.0)

$[\alpha]_D^{22}$=–49.0° (c 0.91, chloroform)

$IR^{KBr}_{max}$ cm$^{-1}$: 3400 (NH), 1690, 1540 (amide), 1100 (ether), 860, 840 (Me$_3$Si), 740, 700 (Ph).

$^1$H-NMR (CDCl$_3$; TMS): δ 7.5–7.1 (m, 45H, 9Ph), 5.48 (s, 1H, PhCH), 4.92 (d, 1H, $J_{1,2}$=3.8 Hz, H-1, fucose portion), 1.51 (s, 3H, AcN), 1.00 (m, 2H, CH$_2$SiMe$_3$), 0.73 (d, 3H, $J_{5,6}$=6.4 Hz, H-6,fucose portion).

$^{19}$F-NMR (CDCl$_3$; CFCl$_3$): δ –207 (ddd, $J_{F,2H}$=51 Hz, $J_{F,3H}$=9.7 Hz, $J_{F,1H}$=3.6 Hz, 2-F).

Mass spectrometry: m/z calculated for $C_{94}H_{108}NO_{19}FSi$ 1603.7381 (M+H); found 1603.7351.

Example 7

Synthesis of 2-(trimethylsilyl)ethyl O-(3,4-di-O-benzyl-2-deoxy-2-fluoro-α-L-fucopyranosyl)-(1→3)-O-(2-acetamide-6-O-benzyl-2-deoxy-β-D-glucopyranosyl: -(1→3)-O-(2,4,6-tri-O-benzyl-β-D-galactopyranosyl)-(1→4)-2,3,6-tri-O-benzyl-β-D-glucopyranoside (referred to as Compound 9 hereinafter).

Compound 8 (125 mg, 0.0779 mmol) was dissolved in 2.5 ml of anhydrous tetrahydrofuran and 400 mg of activated Molecular Sieve 4 Å was added under argon atmosphere. After stirring the mixture at room temperature for 1 hour, 74 mg (1.18 mmol) of sodium borohydrocyanide was added thereto at the same temperature. After cooling the mixture to 0° C., 1.75 ml (1.75 mmol) of 1M hydrochloric acid-ether solution was dropwise added thereto under argon atmosphere. After heating the mixture to room temperature, stirring was continued for 20 minutes and 15 ml of dichloromethane and 3 ml of water were added thereto. Insoluble materials were filtered out and washed with dichloromethane. The filtrate and washing liquids were combined, washed with 2M aqueous hydrochloric acid solution and then with water, and dried over sodium sulfate. After vacuum concentration, the residue was subjected to flash chlomatography with an eluent of n-hexane:ethyl acetate (3:2) to yield Compound 9 (95 mg, 76.0%).

$C_{94}H_{110}NO_{19}FSi$ (1605.0)

$[\alpha]_D^{22}$=–19.5° (c 1.12, chloroform)

$IR^{KBr}_{max}$ cm$^{-1}$: 3700–3200 (OH, NH), 1660, 1500 (amide), 1070 (ether), 860, 840 (Me$_3$Si), 740, 700 (Ph).

$^1$H-NMR (CDCl$_3$; TMS): δ 7.5–7.0 (m, 45H, 9Ph), 1.51 (s, 3H, AcN), 1.14 (d, 3H, $J_{5,6}$=6.4 Hz, H-6, fucose portion), 1.01 (m, 2H, CH$_2$SiMe$_3$).

$^{19}$F-NMR (CDCl$_3$; CFCl$_3$): δ –208 (dd, $J_{F,2H}$=54 Hz, $J_{F,3H}$=6.5 Hz, 2-F).

Mass spectrometry: m/z calculated for $C_{94}H_{110}NO_{19}FSi$ 1605.7537 (M+H); found 1605.7520.

Example 8

Synthesis of 2-(trimethylsilyl)ethyl O-(methyl 5-acetamide-4,7,8,9-tetra-O-acetyl-3,5-dideoxy-D-glycero-α-D-galacto-2-nonuropyranosylonate)-(2→3)-O-(2,4,6--tri-O-benzoyl-β-D-galactopyranosyl)-(1→4)-O-[(3,4-di-O-benzyl-2-deoxy-2-fluoro-α-L-fucopyranosyl)-(1→3)]-O-(2-acetamide-6-O-benzyl-2-deoxy-β-D-glucopyranosyl) -(1→3)-O-(2,4,6-tri-O-benzyl-β-D-galactopyranosyl)-(1→4)-2,3,6-tri-O-benzyl-α-D-glucopyranoside (referred to as Compound 11 hereinafter).

Compound 9 (157 mg, 0.0978 mmol) and methyl O-(methyl 5-acetamide-4,7,8,9-tetra-O-acetyl-3,5-dideoxy-D-glycero-α-D-galacto-2-nonuropyranosylonate)-(2→3)-2,4,6-tri-O-benzoyl-1-thio-β-D-galactopyranoside (Compound 10) (134 mg, 0.135 mmol) were dissolyed in 5 ml of anhydrous dichloromethane and 320 mg of Molecular Sieve 4 Å was added under argon atmosphere. After stirring the mixture at room temperature for 4 hours, 100 mg (0.387 mmol) of dimethyl(methylthio)sulfonium triflate and 100 mg of activated Molecular Sieve 4 Å were added at the same temperature. The reaction mixture was stirred under argon atmosphere at the same temperature for 22 hours. It was cooled with ice and 0.36 ml of methanol and 0.18 ml of triethylamine were added. The mixture was stirred at the same temperature for 30 minutes. After dilution with dichloromethane, filtration and washing, the filtrate and washing liquids were combined and washed with water. After drying over sodium sulfate and concentration under vacuum, the residue was subjected to flash chromatography with an eluent of n-hexane:ethyl acetate (1:3) to yield Compound 11 (98 mg, 39.3%).

$C_{141}H_{159}N_2O_{39}FSi$ (2552.9)

$[\alpha]_D^{24}$=–13.7° (c 1.25, chloroform)

$IR^{KBr}_{max}$ cm$^{-1}$: 3400 (NH), 1740, 1270 (ester), 1690, 1500 (amide), 1070 (ether), 860, 840 (Me$_3$Si), 740, 710 (Ph).

$^1$H-NMR (CDCl$_3$; TMS): δ 8.3–7.0 (m, 60H, 12Ph), 5.67 (m, 1H, H-8, sialic acid portion), 5.43 (dd, 1H, $J_{1,2}$=8.2 Hz, $J_{2,3}$=9.9 Hz, H-2, galactose portion), 5.30 (broad d, 1H, $J_{3,4}$=$J_{4,5}$=3.5 Hz, H-2, galactose portion), 5.23 (dd, 1H, $J_{7,8}$=12.4 Hz, $J_{6,7}$=2.6 Hz, H-7, sialic acid portion), 3.78 (s, 3H, OCH$_3$), 2.43 (dd, 1H, $J_{3e,3a}$=12.7 Hz, $J_{3e,4}$=4.6 Hz, H-3e, sialic acid portion), 2.14, 1.95, 1.92, 1.80 (4s, 12H, 4AcO), 1.53, 1.50 (2s, 6H, 2AcN), 1.09 (d, 3H, $J_{5,6}$=6.4 Hz, H-6, sialic acid portion), 1.01 (m, 2H, Me$_3$SiCH$_2$CH$_2$O).

$^{19}$F-NMR (CDCl$_3$; CFCl$_3$): δ –208 (dd, $J_{F,2H}$=53 Hz, $J_{F,3H}$=7.0 Hz, 2-F).

Mass spectrometry: m/z calculated for $C_{141}H_{159}N_2O_{39}FSi$ 2553.0385 (M+H); found 2553.0404.

Example 9

Synthesis of 2-(trimethylsilyl)ethyl O-(methyl 5-acetamide-4,7,8,9-tetra-O-acetyl-3,5-dideoxy-D-glycero-α-D-galacto-2-nonuropyranosylonate)-(2→3)-O-(2,4,6-tri-O-benzoyl-β-D-galactopyranosyl)-(1→4)-O-[(3,4-di-O-acetyl-2-deoxy-2-fluoro-α-L-fucopyranosyl)-(1→3)]-O-(2-acetamide-6-O-acetyl-2-deoxy-β-D-glucopyranosyl) -(1→3)-O-(2,4,6-tri-O-acetyl-β-D-galactopyranosyl) -(1→4)-2,3,6-tri-O-acetyl-β-D-glucopyranoside (referred to as Compound 12 hereinafter).

Compound 11 (98 mg, 0.038 mmol) was dissolved in 15 ml of ethanol and 5.5 ml of acetic acid, and catalytic reduction was effected in the presence of 90 mg of 10% palladium-carbon under normal hydrogen pressure for 4 days while heating at 45° C. After filtration and vacuum concentration of solvent, 4 ml of pyridine and 2 ml of acetic anhydride were added to the residue and the mixture was stirred at room temperature for 20 hours. After vacuum concentration, the residue was subjected to flash chromatogaphy with an eluent of n-hexane:ethyl acetate (1:6) to yield Compound 12 (66.6 mg, 81.8%).

$C_{96}H_{123}N_2O_{48}FSi$ (2120.1)

$[\alpha]_D^{23}=-23.2°$ (c 0.73, chloroform)

$IR^{KBr}_{max}$ cm$^{-1}$: 3400 (NH), 1740, 1230 (ester), 1700, 1530 (amide), 1070 (ether), 860, 840 (Me$_3$Si), 720 (Ph).

$^1$H-NMR (CDCl$_3$; TMS): δ 8.2–7.4 (m, 15H, 3Ph), 5.66 (m, 1H, H-8, sialic acid portion), 5.27 (dd, 1H, $J_{6,7}$=2.9 Hz, $J_{7,8}$=9.9 Hz, H-7, sialic acid portion), 5.35 (d, 1H, $J_{1,2}$=3.3 Hz, H-1, fucose portion), 5.15 (dd, 1H, $J_{2,3}$=$J_{3,4}$=9.3 Hz, H-3, glucose portion), 4.46 (d, 1H, $J_{1,2}$=7.9 Hz, H-1, glucose portion), 3.80 (s, 3H, OCH$_3$), 3.45 (dd, 1H, $J_{2,3}$=10.0 Hz, $J_{3,4}$=3.5 Hz, H-3, galactose portion), 2.41 (dd, 1H, $J_{3a,3e}$=12.7 Hz, $J_{3e,4}$=4.7 Hz, H-3e, sialic acid portion), 2.13, 2.10, 2.09, 2.08, 2.07, 2.07, 2.06, 2.03, 2.02, 2.00, 1.93, 1.91, 0.91 (13s, 39H, 13AcO), 1.78, 1.56 (2s, 6H, 2AcN), 1.09 (d, 3H, $J_{5,6}$=6.5 Hz, H-6, fucose portion), 0.90 (m, 2H, Me$_3$SiCH$_2$CH$_2$O).

$^{19}$F-NMR (CDCl$_3$; CFCl$_3$): δ −208 (ddd, $J_{F,2H}$=50 Hz, $J_{F,3H}$=7.6 Hz, $J_{F,1H}$=2.5 Hz, 2-F).

Mass spectrometry: m/z calculated for $C_{96}H_{123}N_2O_{48}FSi$ 2120.7110 (M+H); found 2120.7072.

Example 10

Synthesis of O-(methyl 5-acetamide-4,7,8,9-tetra-O-acetyl-3,5-dideoxy-D-glycero-α-D-galacto-2-nonuropyranosylonate)-(2→3)-O-(2,4,6-tri-O-benzoyl-β-D-galactopyranosyl)-(1→4)-O-[(3,4-di-O-acetyl-2-deoxy-2-fluoro-α-L-fucopyranosyl)-(1→3)]-O-(2-acetamide-6-O-acetyl-2-deoxy-β-D-glucopyranosyl)-(1→3)-O-(2,4,6-tri-O-acetyl-β-D-galactopyranosyl)-(1→4)-2,3,6-tri-O-acetyl-D-glucopyranoside (referred to as Compound 13 hereinafter).

Under argon atmosphere, 60 mg (0.028 mmol) of Compound 12 was dissolved in 0.8 ml of anhydrous dichloromethane. The solution was cooled to 0° C. and 1.6 ml of trifluoroacetic acid was dropwise added thereto. After stirring at the same temperature for 5 hours, 2 ml of ethyl acetate was added and the mixture was concentrated at the same temperature under reduced pressure and then vacuum. The residue was subjected to silica gel column chromatography with eluents of dichloromethane to dichloromethane-methanol (30:1 to 20:1) to yield Compound 13 (49.0 mg, 85.7%).

$C_{91}H_{111}N_2O_{48}F$ (2019.8)

$[\alpha]_D^{25}=-9.4°$ (c 0.75, chloroform)

$IR^{KBr}_{max}$ cm$^{-1}$: 3600–3200 (OH, NH), 1740, 1230 (ester), 1670, 1540 (amide), 1070 (ether), 720 (Ph).

Mass spectrometry: m/z calculated for $C_{91}H_{111}N_2O_{48}F$ 2020.6402 (M+H); found 2020.6392.

Example 11

Synthesis of O-(methyl 5-acetamide-4,7,8,9-tetra-O-acetyl-3,5-dideoxy-D-glycero-α-D-galacto-2-nonuropyranosylonate)-(2→3)-O-(2,4,6-tri-O-benzoyl-β-D-galactopyranosyl)-(1→4)-O-[(3,4-di-O-acetyl-2-deoxy-2-fluoro-α-L-fucopyranosyl)-(1→3)]-O-(2-acetamide-6-O-acetyl-2-deoxy-β-D-glucopyranosl)-(1→3)-O-(2,4,6-tri-O-acetyl-β-D-galactopyranosyl)-(1→4)-2,3,6-tri-O-acetyl-α-D-glucopyranosyl trichloroacetoimidate (referred to as Compound 14 hereinafter).

After dissolying 49.0 mg (0.0242 mmol) of Compound 13 in 3 ml of anhydrous dichloromethane, the solution was cooled to 0° C. under argon atmosphere. 0.1 ml (0.997 mmol) of trichloroacetonitrile and then 3 μl (0.02 mmol) of 1,8-diazabicyclo[5.4.0]undec-7-ene (DBU) were added thereto and the mixture was stirred at the same temperature for 3 hours. After vacuum concentration, the residue was subjected to silica gel column chromatography with eluents of dichloromethane to dichloromethane-methanol (40:1 to 20:1) to yield Compound 14 (45.0 mg, 85.9%).

$C_{93}H_{111}N_3O_{48}Cl_3F$ (2164.2)

$[\alpha]_D^{23}=-0.83°$ (c 0.69, chloroform)

$IR^{KBr}_{max}$ cm$^{-1}$: 3400 (NH=C), 1740, 1230 (ester), 1680, 1540 (amide), 1070 (ether), 760, 720 (Ph).

$^1$H-NMR (CDCl$_3$; TMS): δ 8.65 (s, 1H, NH=C), 8.2–7.4 (m, 15H, 3Ph), 6.47 (d, 1H, $J_{1,2}$=3.7 Hz, H-1, glucose portion), 5.66 (m, 1H, H-8, sialic acid portion), 5.36 (d, 1H, $J_{1,2}$=3.8 Hz, H-1, fucose portion), 5.28 (dd, 1H, $J_{6,7}$=2.7 Hz, $J_{7,8}$=9.9 Hz, H-7, sialic acid portion), 3.81 (s, 3H, OCH$_3$), 3.48 (dd, 1H, $J_{2,3}$=9.9 Hz, $J_{3,4}$=4.0 Hz, H-3, galactose portion), 2.41 (dd, 1H, $J_{3a,3e}$=12.7 Hz, $J_{3e,4}$=4.4 Hz, H-3e, sialic acid portion), 2.14, 2.10, 2.10, 2.08, 2.07, 2.07, 2.04, 2.03, 2.00, 1.96, 1.93, 1.92, 1.91 (13s, 39H, 13AcO), 1.78, 1.56 (2s, 6H, 2AcN), 1.10 (d, 3H, $J_{5,6}$=6.5 Hz, H-6, fucose portion), 0.90 (m, 2H, Me$_3$SiCH$_2$CH$_2$O).

$^{19}$F-NMR (CDCl$_3$; CFCl$_3$): δ −209 (dd, $J_{F,2H}$=54 Hz, $J_{F,3H}$=10 Hz, 2-F).

Mass spectrometry: m/z calculated for $C_{93}H_{111}N_3O_{48}Cl_3F$ 2163.5498 (M+H); found 2163.5454.

Example 12

Synthesis of O-(methyl 5-acetamide-4,7,8,9-tetra-O-acetyl-3,5-dideoxy-D-glycero-α-D-galacto-2-nonuropyranosylonate)-(2→3 )-O-(2,4,6-tri-O-benzoyl-β-D-galactopyranosyl)-(1→4)-O-[(3,4-di-O-acetyl-2-deoxy-2-fluoro-α-L-fucopyranosyl)-(1→3)]-O-(2-acetamide-6-O-acetyl-2-deoxy-β-D-glucopyranosyl)-(1→3)-O-(2,4,6-tri-O-acetyl-β-D-galactopyranosyl)-(1→4)-2,3,6-tri-O-acetyl-β-D-glucopyranosyl)-(1→1)-(2S,3R,4E)-2-azide-3-O-benzoyl-4-octadecene-1,3-diol (referred to as Compound 15 hereinafter).

After dissolving 45 mg (0.021 mmol) of Compound 14 and 20 mg (0.047 mmol) of (2S,3R,4E)-2-azide-3-O-benzoyl-4-octadecene-1,3-diol (Compound A) in 1.5 ml of anhydrous dichloromethane, 0.45 g of activated Molecular Sieve 4 Å was added. The mixture was stirred under argon atmosphere at room temperature for 30 minutes and cooled to 0° C. Boron trifluoride-ether complex (0.012 ml, 0.10 mmol) was added and the mixture was stirred at the same temperature for 3 hours. After dilution with dichloromethane, insoluble materials were filtered out and washed with dichloromethane and the filtrate and washing liquids were combined. The organic layer was washed with 1M aqueous sodium bicarbonate solution and then with saturated sodium chloride aqueous solution, and dried over sodium sulfate. After vacuum concentration, the residue was subjected to silica gel column chromatography with eluents of dichloromethane to dichloromethane-methanol (50:1 to 30:1) to yield Compound 15 (36 mg, 71.5%).

$C_{116}H_{148}N_5O_{50}F$ (2431.5)

$[\alpha]_D^{23}=-24.8°$ (c 1.13, chloroform)

$IR^{KBr}_{max}$ cm$^{-1}$: 2950, 2850 (methyl, methylene), 2100 (azide), 1750, 1230 (ester), 1680, 1550 (amide), 1070 (ether), 800, 720 (Ph).

$^1$H-NMR (CDCl$_3$; TMS): δ 8.2–7.4 (m, 15H, 3Ph), 5.91 (dt, 1H, $J_{4,5}$=15.2 Hz, $J_{5,6}$=6.6 Hz, H-5, sphingosine portion), 5.67 (m, 1H, H-8, sialic acid portion), 5.35 (d, 1H, $J_{1,2}$=3.1 Hz, H-1, fucose portion), 5.27 (dd, 1H, $J_{6,7}$=2.7 Hz, $J_{7,8}$=9.9 Hz, H-7, sialic acid portion), 5.14 (dd, 1H, $J_{2,3}$=$J_{3,4}$=9.2 Hz, H-3, glucose portion), 4.49 (d, 1H, $J_{1,2}$=7.7 Hz, H-1, glucose portion), 3.80 (s, 3H, $OCH_3$), 3.44 (dd, 1H, $J_{2,3}$=10.3 Hz, $J_{3,4}$=3.6 Hz, H-3, galactose portion), 2.40 (dd, 1H, $J_{3a,3e}$=12.5 Hz, $J_{3e,4}$=4.4 Hz, H-3e, sialic acid portion), 2.14, 2.11, 2.08, 2.08, 2.07, 2.07, 2.06, 2.04, 2.02, 2.01, 1.94, 1.91, 1.91 (13s, 39H, 13AcO), 1.79, 1.56 (2s, 6H, 2AcN), 1.27 (s, 22H, 11$CH_2$), 1.10 (d, 3H, $J_{5,6}$=6.5 Hz, H-6, fucose portion), 0.87 (t, 3H, J=6.6 Hz, $CH_3CH_2$).

$^{19}$F-NMR ($CDCl_3$; $CFCl_3$): δ −208 (dd, $J_{F,2H}$=51 Hz, $J_{F,3H}$=10Hz, 2-F).

Mass spectrometry: m/z calculated for $C_{116}H_{148}N_5O_{50}F$ 2431.9288 (M+H); found 2431.9258.

Example 13

Synthesis of O-(methyl 5-acetamide-4,7,8,9-tetra-O-acetyl-3,5-dideoxy-D-glycero-α-D-galacto-2-nonuropyranosylonate)-(2→3)-O-(2,4,6-tri-O-benzoyl-β-D-galactopyranosyl)-(1→4)-O-[(3,4-di-O-acetyl-2-deoxy-2-fluoro-α-L-fucopyranosyl)-(1→3)]-O-(2-acetamide -6-O-acetyl-2-deoxy-β-D-glucopyranosyl)-(1→3)-O-(2,4,6-tri-O-acetyl-β-D-galactopyranosyl)-(1→4)-2,3,6-tri-O-acetyl-β-D-glucopyranosyl)-(1→1)-(2S,3R,4E)-3-O-benzoyl-2-tetracosanamide-4-octadecene-1,3-diol (referred to as Compound 16 hereinafter).

Compound 15 (43 mg, 0.018 mmol) was dissolved in a mixed solvent of 4.17 ml of pyridine and 0.83 ml of water and the solution was cooled to 0° C. Hydrogen sulfide gas was passed through the solution for 60 hours. Nitrogen gas was passed through the solution for 10 minutes to remove hydrogen sulfide remaining in the solution. The concentrated residue from the solution was dissolved in 2 ml of anhydrous dichloromethane and cooled to 0° C. Tetracosanoic acid (13 mg, 0.035 mmol) and then 1-ethyl-3-(3-dimethylaminopropyl)carbodiimide, hydrochloride (10 mg, 0.050 mmol) were added and the mixture was stirred at room temperature for 15 hours. It was diluted with dichloromethane, washed with water and dried over sodium sulfate. After vacuum concentration, the residue was subjected to silica gel chromatography with eluents of dichloromethane to dichloromethane-methanol (50:1 to 30:1) to yield Compound 16 (32 mg, 66.0%).

$C_{140}H_{196}N_3O_{51}F$ (2756.1)

$[α]_D^{24}$=−15.3° (c 0.83, chloroform)

$IR^{KBr}_{max}$ cm$^{-1}$: 3400 (NH), 2950, 2850 (methyl, methylene), 1750, 1230 (ester), 1680, 1530 (amide), 1070 (ether), 810, 710 (Ph).

$^1$H-NMR ($CDCl_3$; TMS): δ8.2−7.4 (m, 15H, 3Ph), 5.85 (dt,1H, $J_{4,5}$=14.1 Hz, $J_{5,6}$=6.9 Hz, H-5, sphingosine portion), 5.66 (m, 1H, H-8, sialic acid portion), 5.35 (d, 1H, $J_{1,2}$=2.8 Hz, H-1, fucose portion), 5.27 (dd, 1H, $J_{6,7}$=2.8 Hz, $J_{7,8}$=9.8 Hz, H-7, sialic acid portion), 5.14 (dd, 1H, $J_{2,3}$=$J_{3,4}$=9.3 Hz, H-3, glucose portion), 4.43 (d, 1H, $J_{1,2}$=7.7 Hz, H-1, glucose portion), 3.80 (s, 3H, $OCH_3$), 3.43 (dd, 1H, $J_{2,3}$=10.0Hz, $J_{3,4}$=3.6 Hz, H-3, galactose portion), 2.41 (dd, 1H, $J_{3a,3e}$=12.7 Hz, $J_{3e,4}$=4.7 Hz, H-3e, sialic acid portion), 2.13, 2.10, 2.07, 2.07, 2.07, 2.05, 2.01, 2.00, 2.00, 1.93, 1.93, 1.90, 1.90 (13s, 39H, 13AcO), 1.78, 1.56 (2s, 6H, 2AcN), 1.26 (s, 64H, 32$CH_2$), 1.10 (d, 3H, $J_{5,6}$=6.4 Hz, H-6, fucose portion), 0.87 (t, 6H, J=6.6 Hz, 2$CH_3CH_2$).

$^{19}$F-NMR ($CDCl_3$; $CFCl_3$): δ −208 (dd, $J_{F,2H}$=50 Hz, $J_{F,3H}$=11 Hz, 2-F).

Mass spectrometry: m/z calculated for $C_{140}H_{196}N_3O_{51}F$ 2756.2932 (M+H); found 2756.2867.

Example 14

Synthesis of O-(5-acetamide-3,5-dideoxy-D-glycero-α-D-galacto-2-nonuropyranosylonic acid)-(2→3)-O-β-D-galactopyranosyl-(1→4)-O-[(2-deoxy-2-fluoro-α-L-fucopyranosyl-(1→3)]-O-(2-acetamide-2-deoxy-β-D-glucopyranosyl)-(1→3)-O-β-D-galactopyranosyl-(1→4)-β-D-glucopyranosyl-(1→1)-(2S,3R,4E)-2-tetracosanamide-4-octadecene-1,3-diol (referred to as Compound IX hereinafter).

Compound 16 (33.0 mg, 0.0119 mmol) was dissolved in 2 ml of absolute methanol and 10 mg (0.19 mmol) of sodium methoxide was added under argon atmosphere at room temperature. The mixture was stirred at 40° C. for 24 hours. After allowing it to cool at room temperature, 0.18 ml of water was added and the mixture was stirred for 8 hours. It was passed through a layer of Amberlite IR-120 (H-type) with an eluent of methanol. After vacuum concentration, the residue was subjected to gel filtration column chromatography on Sephadex LH20 (15 g) using chloroform-methanol-water (50:40:7) as an eluent to yield Compound IX (20.6 mg, 66.0%).

$C_{85}H_{152}N_3O_{34}F$ (1779.2)

$[α]_D^{24}$=−16.0° (c 0.35, chloroform-methanol-$H_2O$=50:40:7)

$IR^{KBr}_{max}$ cm$^{-1}$: 3700−3200 (OH, NH), 2920, 2850 (methyl, methylene), 1700 (carboxylic acid), 1650, 1540 (amide), 1070 (ether).

$^1$H-NMR [($CD_3$)$_2$SO—$D_2O$=50:1; TMS]: δ 5.32 (dt,1H, $J_{4,5}$=15.3 Hz, $J_{5,6}$=6.6 Hz, H-5, sphingosine portion), 5.34 (dd, 1H, $J_{3,4}$=7.3 Hz, $J_{4,5}$=15.3 Hz, H-4, sphingosine portion), 5.10 (d, 1H, $J_{1,2}$=3.5 Hz, H-1, fucose portion), 4.74 (d, 1H, $J_{1,2}$=6.8 Hz, H-1, N-acetyl-glucosamine portion), 4.16 (d, 1H, $J_{1,2}$=7.8 Hz, glucose portion), 2.77 (dd, 1H, $J_{3a,3e}$=12.2 Hz, $J_{3e,4}$=4.8 Hz, H-3e, sialic acid portion), 1.89, 1.78 (2s, 6H, 2AcN), 1.23 (s, 64H, 32$CH_2$), 0.96 (d, 3H, $J_{5,6}$=6.3 Hz, H-6, fucose portion), 0.85 (t, 6H, J=6.4 Hz, 2$CH_3CH_2$).

$^{19}$F-NMR [($CD_3$)$_2$SO—$D_2O$=50:1; $CFCl_3$]: δ −208 (dd, $J_{F,2H}$=54 Hz, $J_{F,3H}$=8 Hz, 2-F).

Mass spectrometry: m/z calculated for $C_{85}H_{152}N_3O_{34}F$ 1801.0139 (M+Na); found 1801.0167. elemental analysis: calculated for $C_{85}H_{152}N_3O_{34}F·2.5H_2O·1.75CHCl_3$ C: 51.25, H: 7.87, N: 2.07; found C: 51.18, H: 8.17, N: 2.16.

What is claimed is:

1. A compound represented by the formula (I-1):

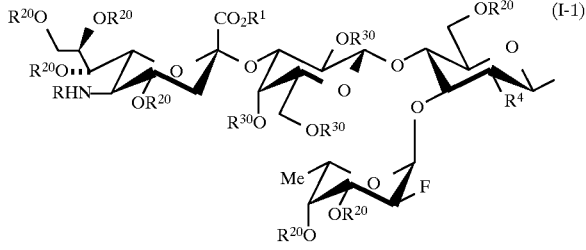

-continued

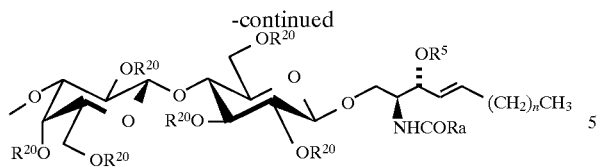

wherein R denotes an aliphatic acyl group having 2 to 6 carbon atoms; $R^1$ denotes a hydrogen atom or a lower alkyl group having 1 to 5 carbon atoms; $R^{20}$, $R^{30}$ and $R^5$ independently denote a hydrogen atom, an aliphatic acyl group having 2 to 6 carbon atoms, or an aromatic acyl group having 7 to 13 carbon atoms; $R^4$ denotes a hydroxy group, an aliphatic acylamino group having 2 to 6 carbon atoms, an aromatic acylamino group having 7 to 13 carbon atoms, an aliphatic acyloxy group having 2 to 6 carbon atoms, or an aromatic acyloxy group having 7 to 13 carbon atoms; Ra denotes a straight or branched, saturated or unsaturated, aliphatic group having 1 to 30 carbon atoms; Me denotes a methyl group; and n denotes an integer of 0 to 20, provided that when $R^1$ is a hydrogen atom, $R^{20}$, $R^{30}$ and $R^5$ all denote a hydrogen atom; and $R^4$ denotes a hydroxy group, or an aliphatic or aromatic acylamino group; or when $R^1$ is a lower alkyl group, $R^{20}$, $R^{30}$ and $R^5$ denote an aliphatic or aromatic acyl group; and $R^4$ denotes an aliphatic or aromatic acylamino group, or an aliphatic or aromatic group.

2. A compound represented by the formula (I-2):

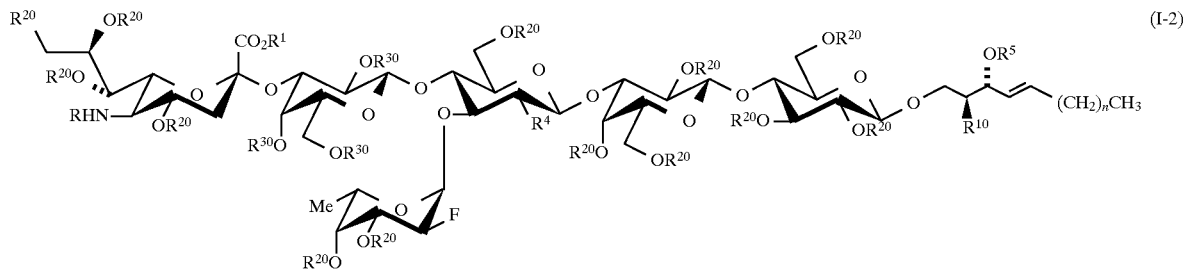

wherein R, $R^1$, $R^{20}$, $R^{30}$, $R^4$, $R^5$, Me and n are as defined in claim 1; and $R^{10}$ denotes a $N_3$ or $NH_2$ group, provided that when $R^1$ is a hydrogen atom, $R^{20}$, $R^{30}$ and $R^5$ all denote a hydrogen atom; and $R^4$ denotes a hydroxy group, or an aliphatic or aromatic acylamino group; or when $R^1$ is a lower alkyl group, $R^{20}$, $R^{30}$ and $R^5$ denote an aliphatic or aromatic acyl group; and $R^4$ denotes an aliphatic or aromatic acylamino group, or an aliphatic or aromatic acyloxy group.

3. A compound represented by the formula (II):

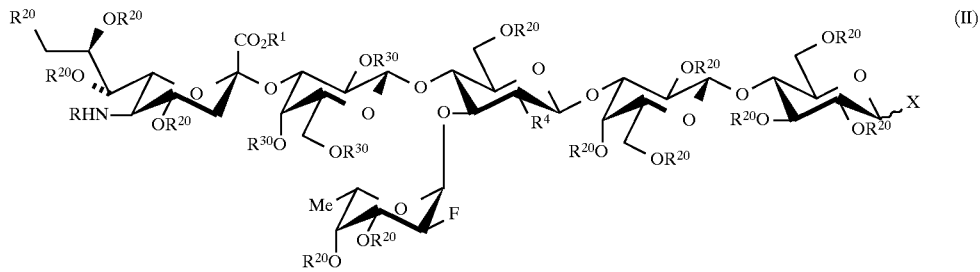

wherein R, $R^1$, $R^{20}$, $R^{30}$, $R^4$ and Me are as defined in claim 1; and X denotes a hydroxy group, a fluorine atom, a thioalkyl group having 1 to 5 carbon atoms, a thioaryl group having 6 to 12 carbon atoms, or a —OC (NH) CCl$_3$ group, provided that when R$^1$ is a hydrogen atom, R$^{20}$ and R$^{30}$ both denote a hydrogen atom; R$^4$ denotes a hydroxy group, or an aliphatic or aromatic acylamino group; and X denotes a hydroxy group; or when R$^1$ is a lower alkyl group, R$^{20}$ and R$^{30}$ denote an aliphatic or aromatic acyl group; R$^4$ denotes an aliphatic or aromatic acylamino group, or an aliphatic or aromatic acyloxy group; and X denotes a fluorine atom, a thioalkyl group, a thioaryl group or a —OC(NH)CCl$_3$ group.

4. A compound represented by the formula (III):

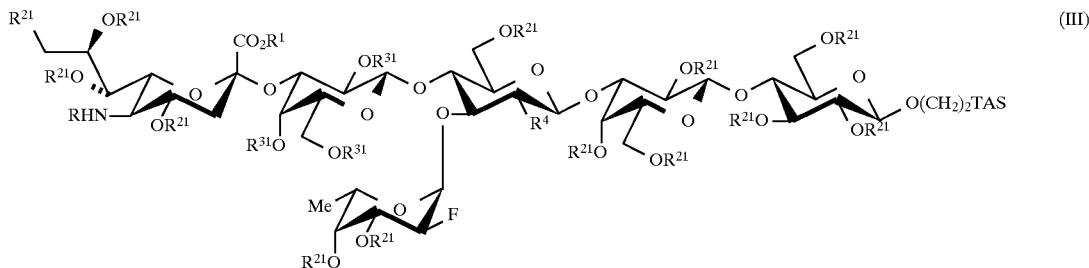

(III)

wherein R, R$^1$, R$^4$ and Me are as defined in claim 1; R$^{21}$ and R$^{31}$ independently denote a hydrogen atom, an unsubstituted or substituted phenylmethyl group having 7 to 13 carbon atoms, an aliphatic acyl group having 2 to 6 carbon atoms, or an aromatic acyl group having 7 to 18 carbon atoms; and TAS denotes a trialkylsilyl group in which the alkyl group has 1 to 7 carbon atoms, provided that when R$^1$ is a hydrogen atom, R$^{21}$ and R$^{31}$ both denote a hydrogen atom; and R$^4$ denotes a hydroxy group or an aliphatic or aromatic acylamino group; or when R$^1$ is a lower alkyl group, R$^{21}$ and R$^{31}$ denote an unsubstituted or substituted phenylmethyl group, or an aliphatic or aromatic acyl group; and R$^4$ denotes an aliphatic or aromatic acylamino group, or an aliphatic or aromatic acyloxy group.

5. A compound represented by the formula (IV):

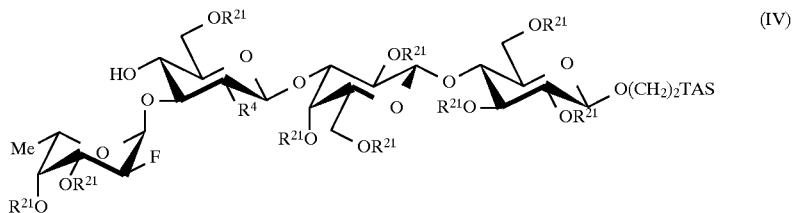

(IV)

wherein R$^{21}$, R$^4$ and TAS are as defined in claim 4, provided that when R$^{21}$ is a hydrogen atom, R$^4$ denotes a hydroxy group, or an aliphatic or aromatic acylamino group; or when R$^{21}$ is an aliphatic or aromatic acyl group, or an unsubstituted or substituted phenylmethyl group, R$^4$ denotes an aliphatic or aromatic acylamino group, or an aliphatic or aromatic acyloxy group.

6. A compound represented by the formula (V):

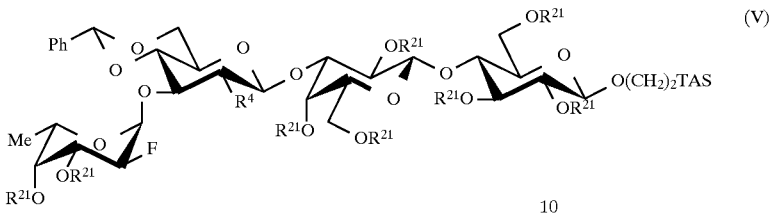

wherein $R^{21}$, $R^4$ and TAS are as defined in claim 4; and Ph denotes an unsubstituted or substituted phenyl group, provided that when $R^{21}$ is a hydrogen atom, $R^4$ denotes a hydroxy group, or an aliphatic or aromatic acylamino group; or when $R^{21}$ is an unsubstituted or substituted phenylmethyl group, or an aliphatic or aromatic acyl group, $R^4$ denotes an aliphatic or aromatic acylamino group, or an aliphatic or aromatic acyloxy group.

7. A compound represented by the formula (VI):

wherein $R^6$ denotes an unsubstituted or substituted phenylmethyl group; and $R^9$ denotes a lower alkyl group having 1 to 5 carbon atoms, or an unsubstituted or substituted phenyl group having 6 to 12 carbon atoms.

8. A process for preparing a compound represented by the formula (VIII):

wherein $R^8$ denotes an aliphatic acyl group having 2 to 6 carbon atoms or an aromatic acyl group having 7 to 13 carbon atoms, comprising reacting a compound represented by the formula:

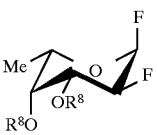

wherein $R^8$ is as defined above, with hydrogen bromide in the presence of acetic acid; or with phosphorus tribromide or phosphorous pentabromide.

* * * * *

UNITED STATES PATENT AND TRADEMARK OFFICE
CERTIFICATE OF CORRRECTION

PATENT NO. : 5,808,018
DATED : September 15, 1998
INVENTOR(S) : Takao Iida, et al.

It is certified that error appears in the above-identified patent and that said Letters Patent is hereby corrected as shown below:

On the title page, item [56], insert the following:

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | WO | 9 | 4 | 0 | 0 | 4 | 7 | 7 | 01/06/1994 | WIPO | | | | |
| | WO | 9 | 2 | 2 | 2 | 5 | 6 | 5 | 12/23/92 | WIPO | | | | |
| | WO | 9 | 4 | 2 | 6 | 7 | 6 | 0 | 11/24/1994 | WIPO | | | | |
| | WO | 9 | 2 | 2 | 2 | 5 | 6 | 4 | 12/23/1992 | WIPO | | | | |

Signed and Sealed this

Twenty-sixth Day of October, 1999

Attest:

Q. TODD DICKINSON

*Attesting Officer*     *Acting Commissioner of Patents and Trademarks*